(12) United States Patent
Huang

(10) Patent No.: US 12,390,553 B2
(45) Date of Patent: Aug. 19, 2025

(54) BIOLOGICAL SCAFFOLD AND METHOD FOR FABRICATING THE SAME

(71) Applicant: National Cheng Kung University, Tainan (TW)

(72) Inventor: Lynn L. H. Huang, Tainan (TW)

(73) Assignee: National Cheng Kung University, Tainan (TW)

( * ) Notice: Subject to any disclaimer, the term of this patent is extended or adjusted under 35 U.S.C. 154(b) by 934 days.

(21) Appl. No.: 17/418,300

(22) PCT Filed: Dec. 30, 2019

(86) PCT No.: PCT/US2019/068907
§ 371 (c)(1),
(2) Date: Jun. 25, 2021

(87) PCT Pub. No.: WO2020/140111
PCT Pub. Date: Jul. 2, 2020

(65) Prior Publication Data
US 2022/0062499 A1 Mar. 3, 2022

Related U.S. Application Data

(60) Provisional application No. 62/785,888, filed on Dec. 28, 2018.

(51) Int. Cl.
| | | |
|---|---|---|
| A61L 27/24 | (2006.01) | |
| A01N 1/00 | (2006.01) | |
| A61K 38/18 | (2006.01) | |
| A61K 47/42 | (2017.01) | |
| A61L 27/34 | (2006.01) | |
| A61L 27/36 | (2006.01) | |
| A61L 27/38 | (2006.01) | |
| A61L 27/54 | (2006.01) | |
| A61L 27/56 | (2006.01) | |

(52) U.S. Cl.
CPC ............... *A61L 27/24* (2013.01); *A01N 1/00* (2013.01); *A61K 47/42* (2013.01); *A61L 27/34* (2013.01); *A61L 27/3687* (2013.01); *A61L 27/3834* (2013.01); *A61L 27/54* (2013.01); *A61L 27/56* (2013.01); *A61K 38/1858* (2013.01); *A61L 2300/406* (2013.01); *A61L 2300/414* (2013.01); *A61L 2420/00* (2013.01)

(58) Field of Classification Search
CPC ...... A61L 27/24; A61L 27/34; A61L 27/3687; A61L 27/3834; A61L 27/54; A61L 27/56; A61L 2300/406; A61L 2300/414; A61L 2400/00; A01N 1/00; A61K 47/42; A61K 38/1858

See application file for complete search history.

(56) References Cited

U.S. PATENT DOCUMENTS

| | | |
|---|---|---|
| 5,192,743 A | 3/1993 | Hsu et al. |
| 5,512,291 A | 4/1996 | Li |
| 6,090,996 A | 7/2000 | Li |
| 9,925,140 B2 | 3/2018 | Huang |
| 2004/0138695 A1 | 7/2004 | Li et al. |
| 2005/0027069 A1 | 2/2005 | Rhee et al. |
| 2005/0042254 A1* | 2/2005 | Freyman ............ A61L 27/3834 424/426 |
| 2006/0068013 A1 | 3/2006 | DiTizio et al. |
| 2008/0089940 A1 | 4/2008 | Omidian et al. |
| 2009/0075933 A1 | 3/2009 | Basu et al. |
| 2009/0305415 A1 | 12/2009 | Huang |
| 2010/0063253 A1 | 3/2010 | Lin et al. |
| 2010/0099623 A1 | 4/2010 | Schroeder et al. |
| 2010/0214815 A1 | 8/2010 | Tam et al. |
| 2010/0215715 A1 | 8/2010 | Han et al. |
| 2011/0091550 A1 | 4/2011 | Zhang et al. |
| 2011/0150823 A1 | 6/2011 | Huang |
| 2011/0262541 A1* | 10/2011 | Lauritzen ............... C07K 14/78 424/93.1 |
| 2011/0276147 A1 | 11/2011 | Cook et al. |
| 2012/0328557 A1 | 12/2012 | Huang |
| 2014/0052518 A1 | 2/2014 | Humphries, IV et al. |
| 2014/0242347 A1 | 8/2014 | Paukshto et al. |
| 2018/0044629 A1* | 2/2018 | Qin ..................... A61L 27/56 |
| 2018/0214606 A1 | 8/2018 | Eklund |
| 2018/0230644 A1 | 8/2018 | Purcell et al. |

FOREIGN PATENT DOCUMENTS

| | | |
|---|---|---|
| EP | 0308238 A1 | 3/1989 |
| JP | 1996325160 | 10/1996 |

OTHER PUBLICATIONS

"Amine-Reactive Crosslinker Chemistry" is pdf of webpage at https://www.thermofisher.com/us/en/home/life-science/protein-biology/protein-biology-learning-center/protein-biology-resource-library/pierce-protein-methods/amine-reactive-crosslinker-chemistry.html #2, accessed Aug. 15, 2021 (Year: 2021).

Chang et al "A Genipin-Crosslinked Gelatin Membrane as Wound-Dressing Material: In Vitro and In Vivo Studies" Journal of Biomaterials Science: Polymer Edition vol. 14, pp. 481-495, 2003.

(Continued)

*Primary Examiner* — Shirley V Gembeh

(74) *Attorney, Agent, or Firm* — Morse, Barnes-Brown & Pendleton, P.C.; Jeannie Wu, Esq.

(57) ABSTRACT

A biological scaffold in the present invention comprises a main body, a biological material layer, and an optional tissue adhesive layer. The main body at least has a non-constituted collagen matrix. The biological material layer is coated at least on a surface of the main body, and the tissue adhesive layer is disposed at least on another surface of the main body. When the biological scaffold is adhered to a tissue through the tissue adhesive layer, a plurality of cells move from the tissue to either the adhesive layer or the biological material layer for tissue repairing or regeneration.

20 Claims, 20 Drawing Sheets

(56) References Cited

OTHER PUBLICATIONS

Chiono et al "Genipin-Crosslinked Chitosan/Gelatin Blends for Biomedical Applications" Journal of Materials Science:Materials in Medicine vol. 19, pp. 889-898, 2008.
Final Office Action in U.S. Appl. No. 16/173,769 dated Aug. 23, 2021.
Final Office Action in U.S. Appl. No. 16/173,769 dated Mar. 23, 2023.
International Search Report for International Application No. PCT/US2011/041629 mailed Mar. 2, 2012.
International Search Report for International Application No. PCT/US2019/068910 mailed Apr. 21, 2020.
International Search Report for International Application No. PCT/US2019/68907 mailed Apr. 29, 2020.
Jung et al "Ex Vivo Expansion of Human Mesenchymal Stem Cells in Defined Serum-Free Media" Stem Cells International vol. 2012, pp. 1-21, 2012.
Kale RN, Bajaj AN, Ultraviolet Spectrophotometric Method for Determination of Gelatin Crosslinking in the Presence of Amino Groups, 1990, J. Young Pharm., vol. 2, No. 1, pp. 90-94 (Year: 1990).
Kanagy, Joseph R., Chemistry of Collagen, 1947, Circular of the National Bureau of Standards C458, United States Government Printing Office, Washington, D.C., USA, pp. 1-28 (1947).
Layman et al "The Effect of the Controlled Release of Basic Fibroblast Growth Factor from Ionic Gelatin-Based Hydrogels on Angiogenesis in a Murine Critical Limb Ischemic Model" Biomaterials vol. 28, pp. 2646-2654, 2007.
Mao et al "The Properties of Chitosan-Gelatin Membranes and Scaffolds Modified with Hyaluronic Acid by Different Methods" Biomaterials vol. 24, pp. 1621-1629, 2003.
Non-Final Office Action in U.S. Appl. No. 16/173,769 dated May 23, 2022.
Non-Final Office Action in U.S. Appl. No. 16/173,769 dated Oct. 30, 2020.
Non-Final Office Action in U.S. Appl. No. 16/173,769 dated Oct. 31, 2023.
Shu, X.Z. et al., "In situ crosslinkable hyaluronan hydrogels for tissue engineering", Biomaterials, vol. 25, pp. 1339-1348, 2004.
Sung et al "Feasibility Study of a Natural Crosslinking Reagent for Biological Tissue Fixation" Journal of Biomedical Materials Research vol. 42, pp. 560-567, 1998.
Sung et al "Felatin-Derived Bioadhesives for Closing Skin Wounds: An In Vivo Study" Journal of Biomaterials Science: Polymer Edition vol. 10, pp. 751-771, 1999.

* cited by examiner

BIOLOGICAL SCAFFOLD AND METHOD FOR FABRICATING THE SAME

CROSS REFERENCE TO RELATED APPLICATIONS

This application is the National Stage of International Application No. PCT/US2019/068907, filed on Dec. 30, 2019, which claims priority to U.S. Provisional Application No. 62/785,888, filed on Dec. 28, 2018. The contents of these applications are hereby incorporated by reference in their entirety.

TECHNICAL FIELD

The present invention provides a biological scaffold, which comprises of a non-reconstituted collagen matrix and a biological material, and optionally, a tissue adhesive layer, and a method for fabricating the same. More particularly, such non-reconstituted collagen matrix and such biological scaffold are useful as dressings to promote wound healing.

BACKGROUND

Tissue engineering refers to reconstituting or repairing organs and tissues through the technique of in vitro culture or construction using synthetic or biologically active substances. Tissue engineering involves multiple disciplines such as biology, material science, and engineering, and has been able to reconstruct tissues such as bone, cartilage, skin, kidney, liver, digestive tract, cornea, muscle, and breast. A basic approach to tissue engineering, also known as "regenerative medicine", consists of the following steps: First, the cells are removed from the human body and the cells are cultured in vitro until reaching sufficient numbers. Then, the cells are placed and grown in an artificial scaffold. Sometimes it is even necessary to add some chemicals or biological factors to promote cell differentiation. Finally, artificial tissues into the patient. Therefore, three elements of tissue regeneration are cells, biological scaffolds, and growth factors.

Among them, the unit that constitutes the most basic structure and function of the human body is the cell. Existing between cells is the extracellular matrix, which is produced by the cells themselves. It is a substance including structural components such as protein fibril/bundle (ex. collagen), crystalline inorganic minerals, and so on.

Tissue consists of many cells with similar morphology and functions and bind together through the extracellular matrix. Among them, they are divided into different tissues according to different cell types, e.g., epithelial tissue, connective tissue, muscular tissue, and nerve tissue, etc. Among them, connective tissue is composed of a large number of extracellular matrix and cells scattered in it. Extracellular matrix contains matrix, fibrils, tissue fluids and so on. Collagen is the most important structural protein in animal connective tissue and the most important component in the extracellular matrix. In animal connective tissue, in addition to 60-70% of water, it contains 20-30% of collagen. Therefore, collagen is a protein widely present in animals, and connective tissue is widely distributed in the human body and found in almost all organs.

Collagen exists mainly in the form of insoluble fibril, accounting for about 33% of the protein in human tissues. In other words, collagen accounts for one-third of the protein in the human body and is a very important structural protein in connective tissues. It plays the role of "mattress" and "cement", which protects and links various tissues to support the structure of the human body. Therefore, collagen is commonly used as a material for bioprosthesis.

The most basic unit of collagen is tropocollagen, which is a molecule composed of three polypeptide chains. The three polypeptide chains are tightly bound together parallelly by interchain hydrogen bonds to form a stable triple-helix structure. The collagen unit of the triple-helix chain is called tropocollagen with a diameter of about 1.5 nm and a length of about 280 nm. In a physiological state, multiple tropocollagen molecules self-aggregate into a collagen microfibril structure, with each molecule staggered at a distance of about 67 nm. The microfibrils can then be aggregated into fibrils of varied diameters, usually about 50 nm. In the body, the fibrils are stacked into different quadary structures, which may form reticular fibrils such as the matrix under epidermal cells. These fibrils may further aggregate into fibers, like ligaments and tendons containing regularly arranged collagen fibrils in a single direction.

So far, animal collagens that have been discovered can be divided into at least 28 types. Except for hyaline cartilage, which is mainly type II collagen, most connective tissues contain mainly type I collagen, accounting for about 90% of the total collagen content, and is also the most widely used collagen biomaterial. Its main structural protein gives the connective tissue the support, protection, and various mechanical properties required for connective tissue, such as tension, tensile, strength, and viscoelasticity, etc. In terms of biochemical properties, it can promote coagulation cascade and catalyze the formation of blood clots. The functions of collagen include controlling molecular permeability, promoting wound healing and tissue repair, and regulating the physiological functions of cells and tissues.

A method for preparing a conventional collagen matrix, such as the method for preparing a porous collagen matrix in the Chinese Patent No. 476642, is to reconstitute collagen matrix at 30-45° C. with a similar physiological condition. A porous collagen matrix can be obtained by freezing and lyophilizing such matrix. FIG. 3 shows an electron micrograph with 100× magnification of a conventional porous collagen matrix. The appearance of which has a structure that exhibits a loose and irregular flaky appearance and does not provide better tension and anti-cell contractility, which are required for optimizing migration and proliferation of suitable cells. Furthermore, due to the surface characteristics of collagen, it is also detrimental to cell entry.

Another conventional technique of "Dural/meningeal repair product using collagen matrix" in U.S. Pat. No. 5,997,895 provides a method for repairing and promoting meninge growth. A proven biocompatible source of collagen having no pathogenic virus residues can be used. A cross-linking reaction is used on the collagen matrix and a porous collagen structure is formed with a porous diameter of 10-500 μm, which allows damaged meninges to repair and promoted the growth of meninges. However, since the collagen is taken from a dermal layer of an animal skin such as pig skin or the like, when the hair follicles are not removed completely during the processing of the pig skin, the overall structure of the subsequent preparation of the collagen matrix would be destroyed. Also, the purity of the prepared collagen would be affected, which may lead to bacterial infection and immune reaction, or cause immune rejection in clinical use.

The Taiwan Patent No. 098125217 entitled "Preparation of high purity collagen" provides a method for collagen preparation comprising of: providing a connective tissue with a surface area of 20 $mm^2$ to 2 $m^2$; using a first acid solution to expand the volume of the connective tissue by at least 50% to form a swollen connective tissue, wherein the pH value of the acid solution is 1-6 and substantially the acid solution does not contain salts; washing the swollen connective tissue to remove non-collagenous substances to form a collagen matrix; and then extracting collagen from the collagen matrix using an extraction solution to make a collagen-containing solution. In the above-mentioned technology, the solution is collagen, and a porous collagen matrix formed through conventional method does not provide better tension and anti-contractility by cells, which are required for optimizing infiltration and proliferation of suitable cells.

Another US invention patent publication number U.S. Pat. No. 8,067,149B2 entitled "Acellular dermal matrix and method of use thereof for grafting" provides a method for extracting an acellular tissue matrix and includes removing hair follicles and extracting with a surfactant SDS. However, it extracts an acellular tissue matrix, which is different from the porous high-purity collagen matrix of the present invention.

The current general state of biological scaffolds is as follows.

At present, most of the biological scaffolds on the market are made of reconstituted collagen matrix, and its related products have been disclosed in many previous patents. For example, in U.S. Pat. No. 4,193,813, collagen is first dissolved in acetic acid, cross-linked with glutaraldehyde, and then frozen at low temperature for a long time (e.g., 20 hours). After thawing, water is mechanically removed to form a sponge-like matrix, and the pore size of the matrix obtained by this method is about 80-1400 μm. U.S. Pat. No. 4,412,947 teaches a method of suspending high-purity insoluble collagen particulates in an acetic acid solution, freezing to −65° C. at a cooling rate of about 0.3 to 0.4° C. per minute, and lyophilizing to form a porous sheet substrate. U.S. Pat. No. 4,522,753 teaches mixing collagen and chondroitin sulfate into a copolymer, cross-linking by glutaraldehyde and lyophilizing to obtain a porous matrix with a pore size of about 20 to 180 μm, which can be used as artificial skin substrate. U.S. Pat. No. 4,970,298 discloses that a mixture solution containing an acid soluble collagen solution or a solution of acid soluble collagen, hyaluronan, and fibronectin, etc. can be crosslinked by carbodiimide and a dehydrothermal method. After freezing at different temperatures, lyophilization is used to make a porous matrix. The freezing temperature is −30 to −50° C., the pore size of the obtained matrix is about 50 to 250 μm, and the collagen matrix containing hyaluronan or fibronectin has a pore size of 100-150 μm. The methods for preparing a collagen matrix disclosed in the above patents mainly use acidic or alkaline collagen crosslinked at a high temperature or by a chemical crosslinking agent and then lyophilize to produce pores to obtain a porous matrix. The matrices prepared by these methods have poor uniformity of pores and difficult control of pore sizes. Moreover, most of the chemical crosslinkers used are toxic. The reconstituted collagen microfibrils or fibrils give the matrix limited support, protection and various mechanical properties, such as tension, tensile, strength, and viscoelasticity, and are thus not very ideal for clinical applications.

The non-reconstituted collagen matrix has high industrial value for clinical applications, and the manufacturing process of the non-reconstituted collagen matrix is disclosed by a U.S. Pat. No. 8,198,408 entitled: "Method for preparing porous collagen matrices" previously applied by the inventor.

Conventionally, a method used in the prior arts, such as the Republic of China Invention Patent No. 150746 entitled "Preparation of a porous collagen matrix", the method initially brings collagen into a neutral solution at 30 to 45° C. for a period of time to allow collagen microfibril reorganization to obtain a gelatinous collagen matrix. The gelatinous collagen matrix is frozen to an appropriate low temperature by an appropriate cooling rate of temperature, and then lyophilized under reduced pressure to obtain a porous collagen matrix. In the Republic of China Patent No. I284665 entitled "Process for preparing porous collagen matrix from connective tissue", a connective tissue substantially treated in situ is subjected to a porous treatment step after a washing step to remove impurities and non-collagen from the connective tissue, in which the porous treatment step is to obtain a collagen matrix with porous properties. Its in-situ treatment omits the conventional procedure of shredding or mincing connective tissue, and the process does not require the use of a cross-linking agent. This method is more convenient for the preparation of a collagen matrix by omitting 2 or 3 treatment steps, but the porous structure and its bearing stress and tension are not described.

In general, if there is a wound on the surface of the human body, gauze, bandages, patches, and medical tapes, etc. are used to cover and wrap the wound to prevent infection by external bacteria. However, the external dressing mentioned above can only quench external bacteria and does not directly help the wound itself.

In summary, in order to solve the problem of preventing wounds from being infected by external bacteria and obtaining porous and high purity collagen, the present invention provides a biological scaffold with non-reconstituted collagen matrix for wound dressing.

SUMMARY OF THE INVENTION

The present invention provides a biological scaffold comprising at least one non-reconstituted collagen matrix and at least one biological material, the biological material uniformly covering at least one surface or both the outer and inner surfaces of the non-reconstituted collagen matrix. Also, a method for preparing the aforementioned non-reconstituted collagen matrix and biological scaffold, which has higher strength than a traditional collagen matrix, is also disclosed in the present invention. Furthermore, because the biological scaffold provided by the present invention can be evenly coated with a biological material layer, it can facilitate the infiltration of cells into the non-reconstituted collagen matrix. In addition, the hair follicle tissue in this non-reconstituted collagen matrix can be destroyed without destroying the main structure of the dermal collagen, thereby resulting in a non-reconstituted collagen matrix having a higher strength than a matrix made by conventional techniques. It also reduces the immune response caused by hair follicles and helps cell growth, making this biological scaffold more suitable for further use in surgery, repairing of human organs and tissues, regenerative medicine, skin transplantation or cosmetic medicine. It can also be used as surgical repair mesh fabric, dental repair mesh fabric, human skin substitute, artificial meningeal substitute, orthopedic repair substitute or wound dressing substitute.

The biological scaffold provided by the present invention includes at least a non-reconstituted collagen matrix and at least one biological material. The non-reconstituted collagen matrix system has a plurality of bundled collagen fibrils and a plurality of pores formed by the bundled collagen fibrils. The biological material is coated on at least one outer surface of the main body and/or the outer surfaces of the bundled collagen fibrils. As the plurality of pores is formed by the bundled collagen fibrils, i.e., the collagen fibrils form the inner walls of the pores, coating the surfaces of the collagen fibrils can be equivalent to coating the inner walls of the pores.

A method of preparing a non-constituted collagen matrix can include: obtaining a dermal layer sheet from an animal skin tissue; carrying out a depilating step that includes immersing the dermal layer sheet in a high ionic strength salt solution and then adding a proteolytic enzyme to the salt solution, whereby a depilated dermal layer sheet is produced; and carrying out a swelling step that includes immersing the depilated dermal layer sheet in a first acidic solution for a sufficient period of time the depilated dermal layer sheet to form a swelled dermal sheet layer, whereby forming a non-reconstituted collagen matrix, the non-reconstituted collagen matrix having a plurality of bundled collagen fibrils that are interwoven and overlapped and a plurality of pores formed by the bundled collagen fibrils.

Optionally, the method for preparing a non-constituted collagen matrix can further include a disinfection step, a degreasing step, a de-antigen step, and/or a strengthening step.

A method for preparing a biological scaffold can include: providing a non-reconstituted collagen matrix described herein; contacting the non-reconstituted collagen matrix with a solution containing a biological material under a decompression environment, whereby the biological material is coated on a first outer surface and inside the plurality of pores of the non-reconstituted collagen matrix.

In conclusion, the preparation method of the present invention can further comprise a disinfection treatment step before or after performing any step, and the sheet or dermal layer sheet is washed with a disinfection solution. Most preferably, the disinfection solution is a peracetic acid solution.

In an embodiment of the present invention, the preparation method provided by the present invention further includes the following steps: first, take out a non-reconstituted collagen matrix coated with the biological material. Next, a cell culture medium is injected into the pores; then, a solution containing a cell is injected so that the cell enters the pore and adhere to the biological scaffold. Preferably, the cell can be a stem cell, satellite cell, precursor cell or tissue cell.

In one embodiment of the method for preparing a non-reconstituted collagen matrix according to the present invention, the animal skin tissue is a pigskin, cowhide or sheepskin tissue.

In one embodiment of the method for preparing a non-reconstituted collagen matrix according to the present invention, the salt solution containing high ionic strength is a salt solution in which anions and cations are combined by an ionic bond. Preferably, the ionic strength of the salt solution containing high ionic strength is greater than 0.15N. Most preferably, the ionic strength of the salt solution containing high ionic strength is between 0.5N-10N. Most preferably, the salt solution containing high ionic strength is a solution containing sodium chloride, ammonium sulfate and a mixture of the above compounds. This high salt condition stabilizes the structure of the non-reconstituted collagen matrix, does not cause it to swell and is extruded into the hair follicle, so that the enzyme can smoothly enter the hair follicle for reaction.

In one embodiment of the method for preparing a non-reconstituted collagen matrix according to the present invention, the proteolytic enzyme can act on the salt solution containing high ionic strength. Preferably, the proteolytic enzyme is selected from the group consisting of serine proteases, threonine proteases, cysteine proteases, aspartate proteases, glutamate proteases, metalloproteases, and combination of the above enzymes. Preferably, the cysteine enzyme is selected from the group consisting of a papaya enzyme (e.g., papain), a pineapple enzyme (e.g., bromelain), and mixture of the above enzymes. Most preferably, the metalloprotease is a dispase.

In one embodiment of the method for preparing a non-reconstituted collagen matrix according to the present invention, a degreasing step is further included before or after the depilation treatment step. The degreasing step is a saponification treatment, an organic solvent treatment, or a combination thereof. In the saponification step, an alkaline substance is used to contact a surface of the dermal layer sheet. Preferably, the alkaline substance is a granular and a strong alkaline particle. Most preferably, the strong base particles are sodium hydroxide particles. The organic solvent treatment is an alcohol treatment, a hexane treatment, or a chloroform treatment.

In one embodiment of the method for preparing a non-reconstituted collagen matrix according to the present invention, the depilation treatment step or any step thereafter further comprises performing a shaking or agitation step. Preferably, the shaking or the agitation step is an ultrasonic oscillating treatment.

In one embodiment of the method for preparing a non-reconstituted collagen matrix according to the present invention, the depilation treatment step or any step thereafter further includes performing a heat treatment. Optimally, the heat treatment is heating to 25° C. to 40° C.

In one embodiment of the method for preparing a non-reconstituted collagen matrix according to the present invention, any step after performing the depilation treatment step further includes a washing step in which the sheet or dermal layer sheet is dipped in a washing solution or passed through a disinfectant gas. Preferably, the washing solution is a phosphate solution or an aqueous solution. Preferably, the disinfecting gas is ozone.

In one embodiment of the method for preparing a non-reconstituted collagen matrix according to the present invention, the first acidic solution is a weak acid solution.

In one embodiment of the method for preparing a non-reconstituted collagen matrix according to the present invention, after the swelling treatment step, further includes a de-antigen treatment step. The de-antigen treatment step is to immerse the sheet or dermal layer sheet in a second acidic solution. The second acidic solution contains a pepsin. Most preferably, the second acidic solution is a weak acidic solution.

In one embodiment of the method for preparing a non-reconstituted collagen matrix according to the present invention, after the swelling treatment step, a strengthening treatment step is further included. The sheet or dermal layer sheet is immersed in an additive. Preferably, the additive is a cross-linking agent solution.

In one embodiment of the present invention, the cross-linking reagent is transglutaminase or acts through the functional groups, wherein one functional group of the cross-linking agent is selected from the group consisting of amine, sulfhydryl, carbonyl, glycol, hydroxyl, carboxyl, azide, imidoester, epoxide, aldehyde, haloacetyl, pyridyl disulfide, pyridyldithiol, hydrazide, photo-reacting, carbodiimide, diazirine, aziridine, acryloyl, arylate, thiol, genipin, riboflavin, flavonoid and its derivatives, hydroxymethyl phosphine, isocyanate, maleimide, 6-maleimidohexanoic acid active ester, disuccinimidyl suberate, bis(sulfosuccinimidyl)suberate, N-hydroxy-succinimide ester (NHS-ester), sulfosuccinimidyl-4-(N-maleimidomethyl)cyclohexane-1-carboxylate, pentafluorophenyl ester (PFP-ester), ethylene glycol diglycidyl ether, glutaraldehyde, 2,3-dibromopropionyl N-hydroxysuccinimide ester, sulfo-N-hydroxysuccinimide ester, chlorambucil-N-hydroxysuccinimide ester, 1-ethyl-3-(3-dimethylaminopropyl) carbodiimide, psoralen, vinyl sulfone, and a combination thereof.

In an embodiment of the present invention, the walls of the plurality of pores in the main body include a structure in which the bundled collagen fibrils are interwoven and overlapped.

In one embodiment of the present invention, the biological scaffold includes at least: a main body including a non-reconstituted collagen matrix, a biological material coated on at least a first surface of the main body, and a tissue adhesive layer on another surface of the main body opposite the first surface, or adjacent the first surface, or on two or more surfaces other than the first surface, wherein the tissue adhesive layer comprises a tissue adhesive. Wherein, when the biological scaffold is adhered to a tissue by the tissue adhesive layer, a plurality of cells moved from the tissue adhesive layer to the biological material layer to perform reconstruction of the tissue.

In one embodiment of the present invention, the biological material is selected from the group consisting of a cell attachment material, a tissue repair material, a cell induction material, a growth factor material, an antibacterial material, and a mixture of the above substances.

Preferably, the cell attachment material may be a saccharide material, a peptide, a protein, a phospholipid, or a combination thereof.

Preferably, the saccharide material may be a glycosaminoglycan material.

Preferably, the glycosaminoglycan material is selected from the group consisting of chondroitin, chondroitin sulfate, heparin, heparan sulfate, heparan sulfate proteoglycan, keratan, keratan sulfate, dermatan sulfate, carrageenan, hyaluronan, and a combination thereof.

Preferably, the tissue repair material may be a biomaterial, an extracellular matrix, a nutrient, and a combination thereof.

Preferably, the biomaterial is selected from the group consisting of collagen, gelatin, elastin, glycosaminoglycan, chitosan, alginate, polyglutamic acid ($\gamma$-PGA), polylysine, poly(lactic-co-glycolic acid) (PLGA), silk fibroin, etc., and a combination thereof.

Preferably, the extracellular matrix is selected from the group consisting of collagen, gelatin, elastin, glycosaminoglycan, proteoglycan, glycoprotein, fibronectin, laminin, aggrecan, metalloproteinase, etc., and a combination thereof.

Preferably, the nutrient is selected from the group consisting of a vitamin, a mineral, a protein, a lipid, a carbohydrate, an amino acid, a peptide, a nucleotide, a deoxynucleotide, a herbal medicine, etc., and a combination thereof.

Preferably, the cell induction material is selected from the group consisting of molecules such as a vitamin, mineral, chemical, medicine, herbal medicine, metabolite, intermediate metabolite, saccharide, peptide, protein, phospholipid, or a combination thereof.

Preferably, the antibacterial material is an antibiotic, an antimicrobial protein, or an antimicrobial peptide.

Preferably, the growth factor material is selected from the group consisting of epidermal growth factor (EGF), fibroblast growth factor (FGF), vascular endothelial growth factor (VEGF), connective tissue growth factor (CTGF), platelet-derived growth factor (PDGF), insulin-like growth factor (IGF-I, IGF-II), nerve growth factor (NGF), hepatocyte growth factor (HGF), colony-stimulating factor (CSF), stem cell factor (SCF), keratinocyte growth factor (KGF), granulocyte colony-stimulating factor (GCSF), macrophage colony-stimulating factor (MCSF), granulocyte macrophage colony-stimulating factor (GMCSF), glial derived neurotrophic factor (GDNF), ciliary neurotrophic factor (CNF), endothelial-monocyte activating polypeptide, epithelial neutrophil activating peptide, erythropoietin, bone morphogenetic protein (BMP-1, BMP-2, BMP-3, etc.), brain-derived neurotrophic factor (BDNF), BRAK, serotonin, von Willebrand factor (vWF), transforming growth factor (TGF-$\alpha$, TGF-$\beta$), interleukin (IL-1, IL-2, IL-3, etc.), tumor necrosis factor (TNF), and a combination thereof.

In one embodiment of the present invention, the biological scaffold provided by the present invention further includes a cell culture medium in the pores.

Preferably, it further comprises a cell, wherein the cell is adhered to the biological scaffold in any one of the pores.

Preferably, the cell can be a stem cell, satellite cell, precursor cell or tissue cell.

In one embodiment of the present invention, the reduced pressure environment is completed by a vacuuming action.

In one embodiment of the present invention, the tissue adhesive layer includes: a cross-linking agent being transglutaminase or containing at least a functional group; one matrix component, the non-reconstituted collagen matrix itself or in addition of a matrix molecule, which is cross-linked with the cross-linking agent; and a quenching agent which is used to react with the functional group of the crosslinking agent or the left-over functional group of the crosslinking agent in order to reduce the cytotoxicity.

Preferably, the matrix molecule is selected from the group consisting of collagen, hyaluronan, gelatin, silk fibroin, fibronectin, elastin, tenascin, laminin, vitronectin, heparan sulfate, chondroitin, chondroitin sulfate, keratin, keratan sulfate, dermatan sulfate, carrageenan, heparin, chitin, chitosan, alginate, aggrecan, agarose, agar, cellulose, methyl cellulose, carboxyl methyl cellulose, glycogen, fibrin, fibrinogen, thrombin, polyglutamic acid, polylysine, polyamino acid, synthetic polymers (e.g., acrylate, polylactic acid, polyglycolic acid, polylactic acid-glycolic acid), a derivative thereof, and a combination thereof.

Preferably, the quenching agent is selected from the group consisting of amino acid, oligopeptide, polypeptide, protein, amine, diamine, oligoamine, polyamine, carbonyl compound, glycol compound, carboxyl compound, dicarboxylate, oligo-carboxylate, polycarboxylate, sulfhydryl compound, oligosulfhydryl compound, polysulfhydryl compound, hydroxyl compound, oligohydroxyl compound, polyhydroxyl compound, saccharide, oligosaccharide, polysaccharides, ribonucleic acid (RNA), deoxyribonucleic acid (DNA), oligonucleotide, azide, photo-crosslinking compound, and a group consisting of a monofunctional or heterobifunctional group, and a combination thereof.

Preferably, the tissue is a skin tissue.

BRIEF DESCRIPTION OF SCHEMA/FIGURE

Figure 7A:
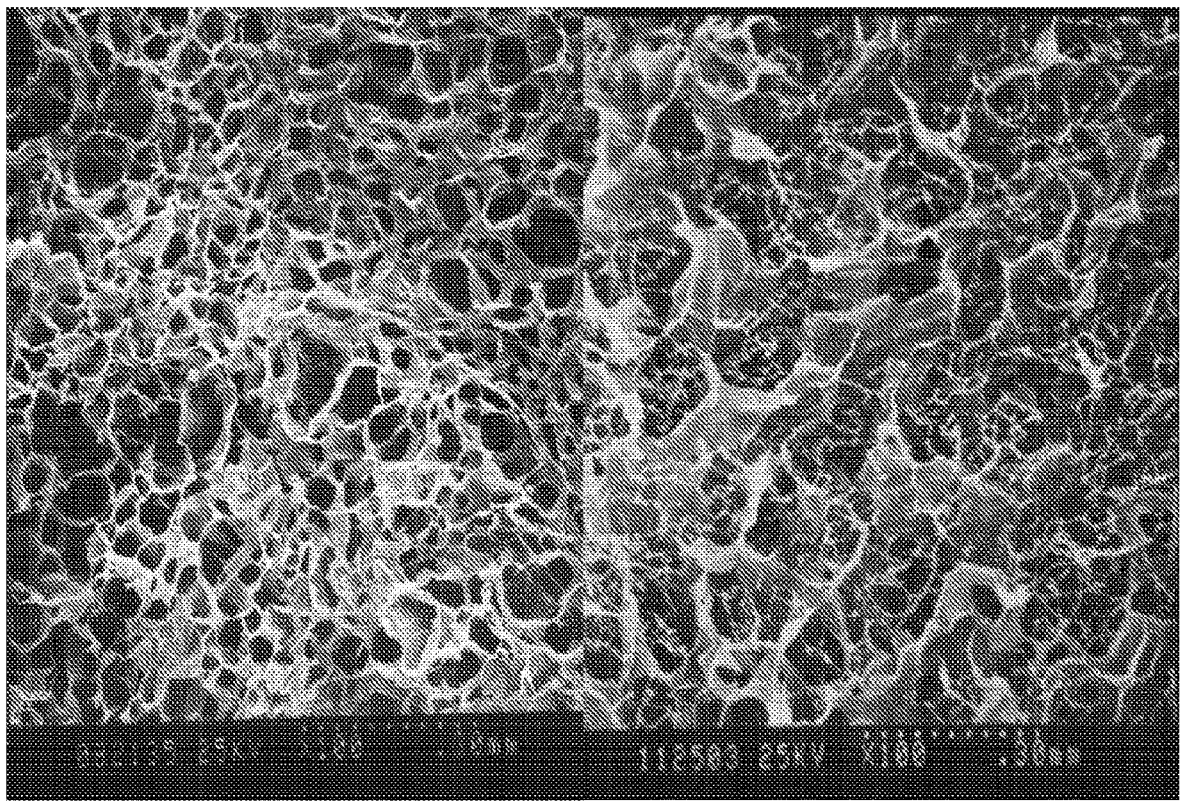
FIGS. 7A to 7B show electron microscope images of a biological scaffold from an embodiment of the present invention.
Figure 7B:
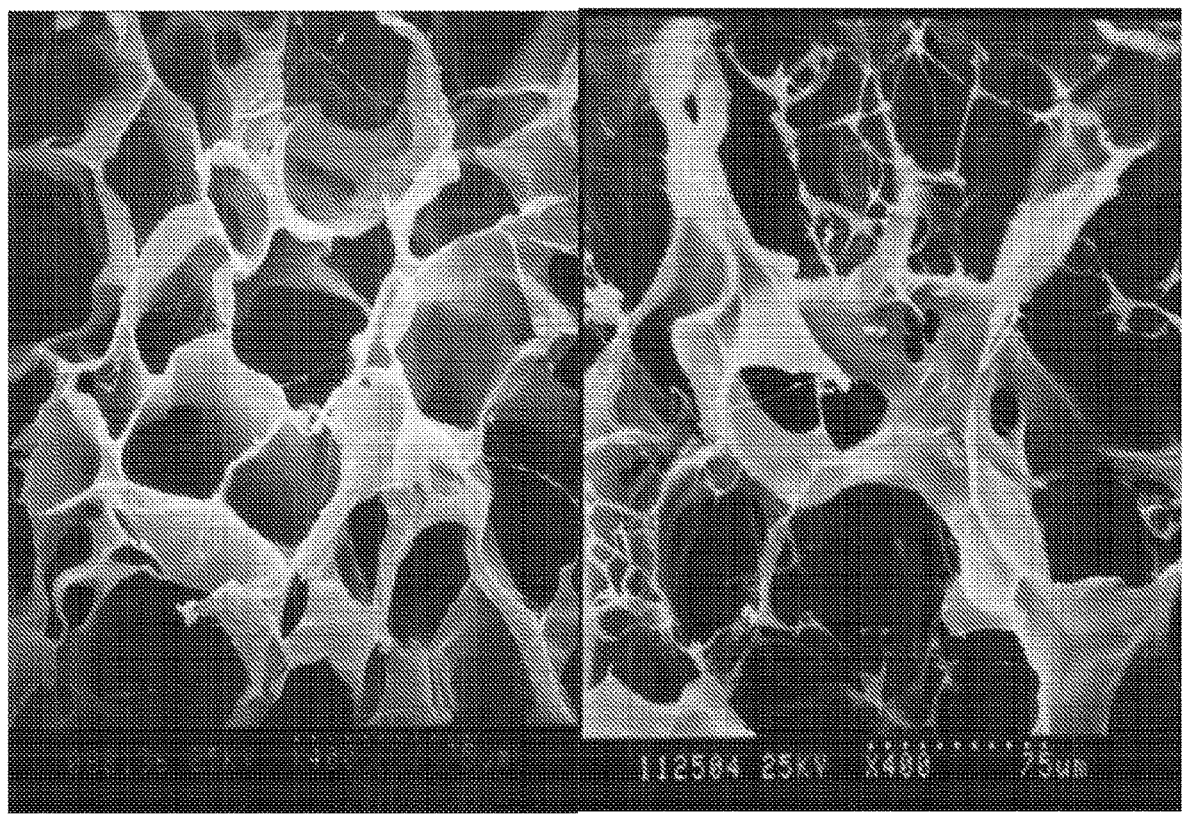
Figure 7C:
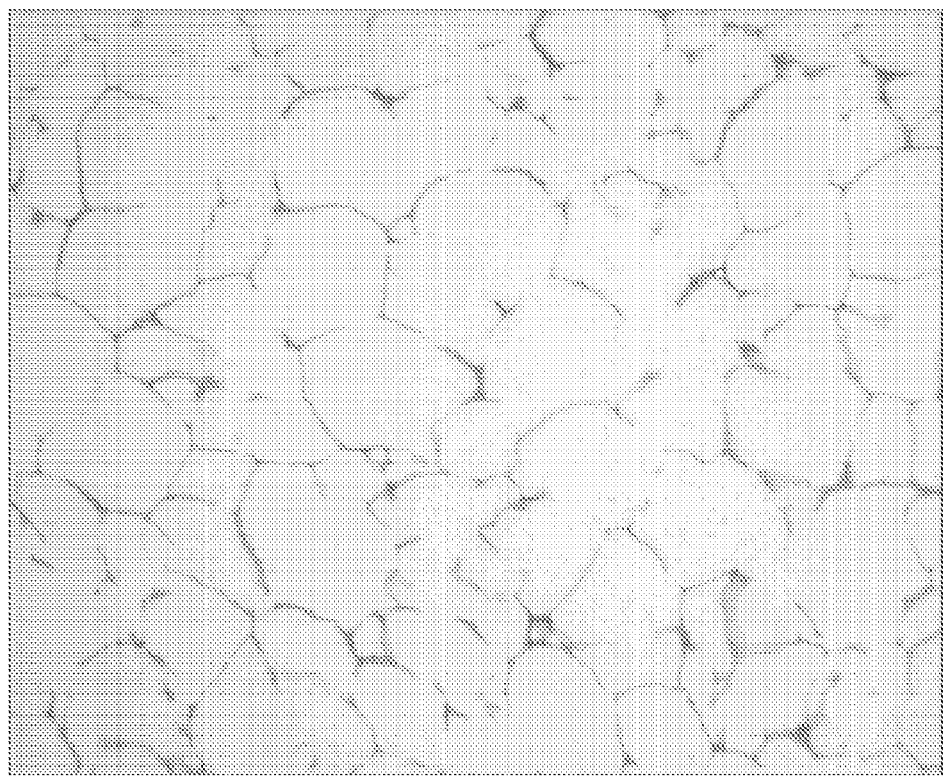

FIG. 7C demonstrates alcian blue staining indicating well-distribution of hyaluronan inside the biological scaffold.

Figure 8:
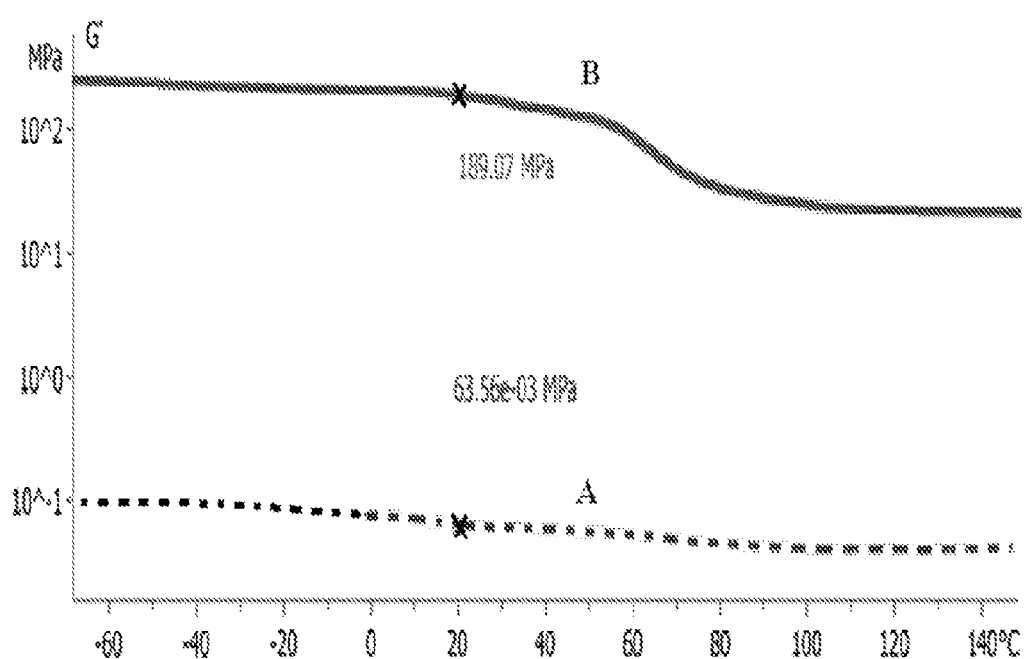

FIG. 8 shows a comparison diagram of a shear stress test between biological scaffolds from an embodiment of the present invention and from a conventional technique.

Figure 9A:
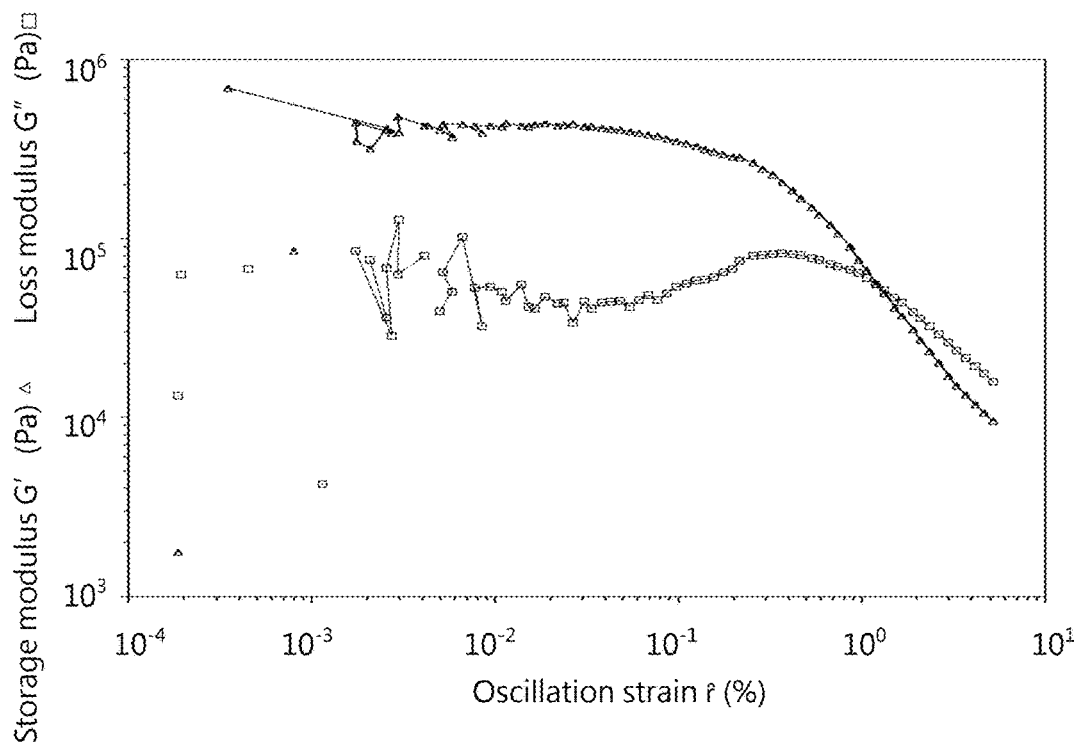
Figure 9B:
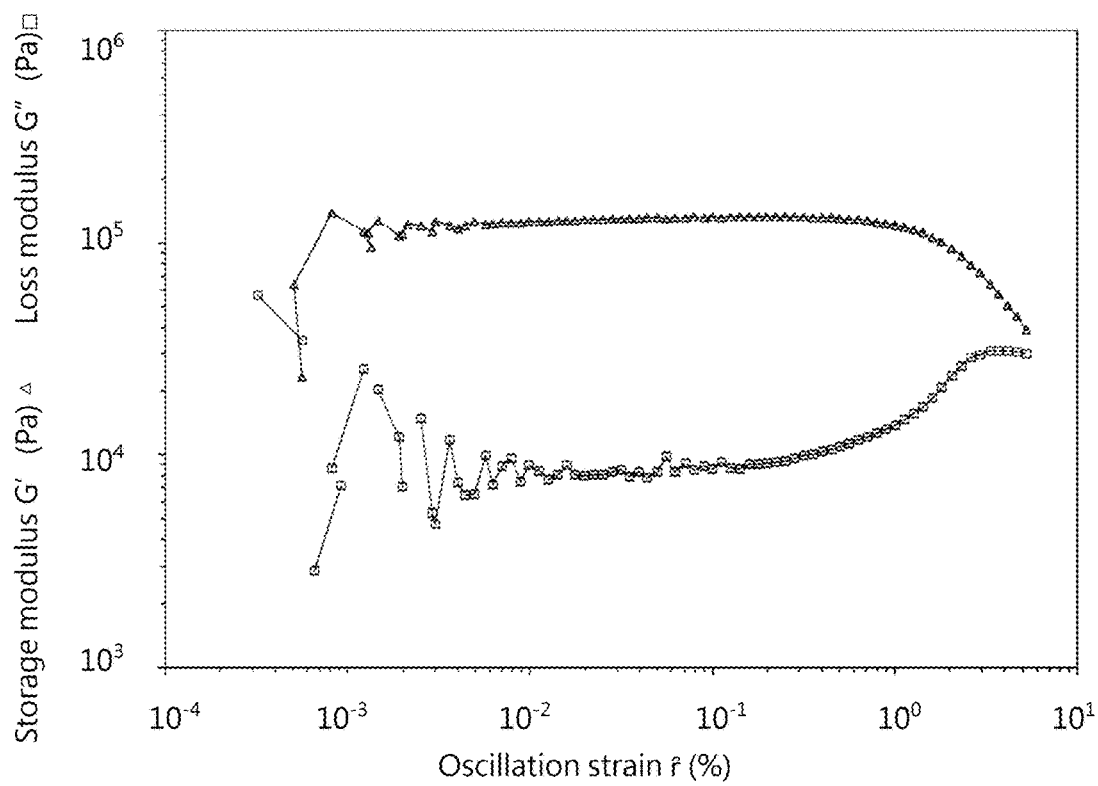

FIGS. 9A and 9B show the storage and loss modulus of a non-reconstituted porous collagen matrix of the present invention and a reconstituted porous collagen matrix from a conventional technique.

Figure 10:
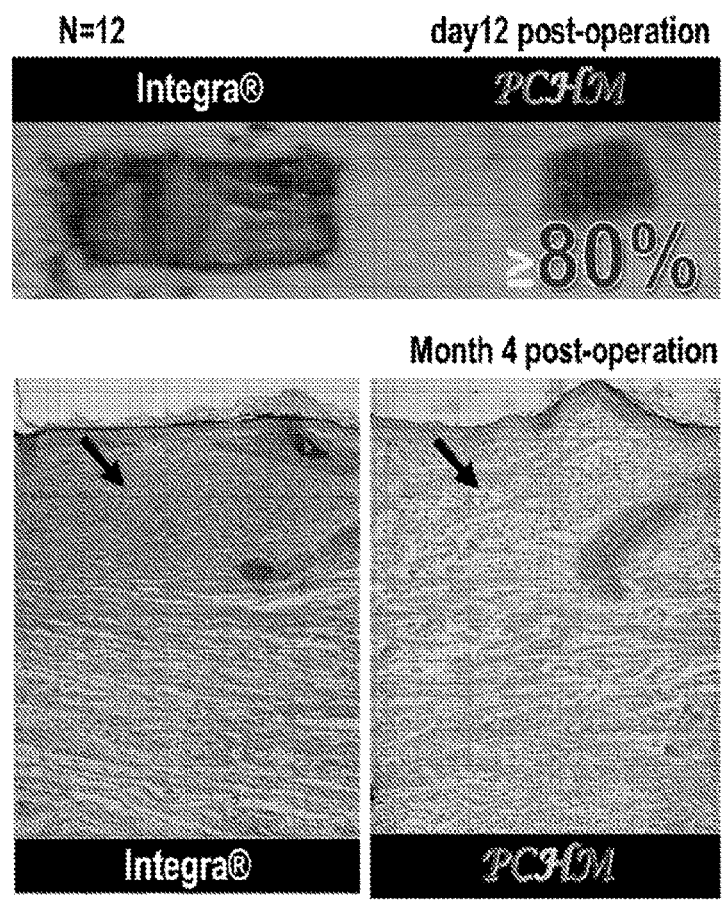
Figure 10:
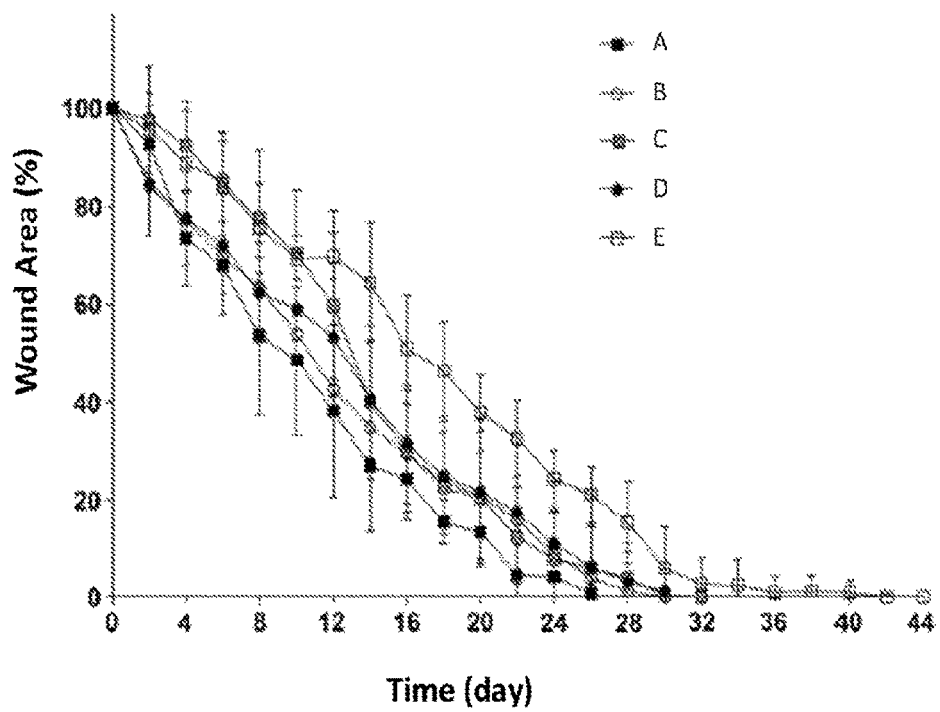

FIG. 10A is a comparison diagram showing the healing of wounds of a biological scaffold in present invention and a reconstituted porous collagen-chondroitin sulfate matrix prepared by a conventional method.

FIG. 10B is a graph showing healing of wounds under different treatments.

Figure 11:
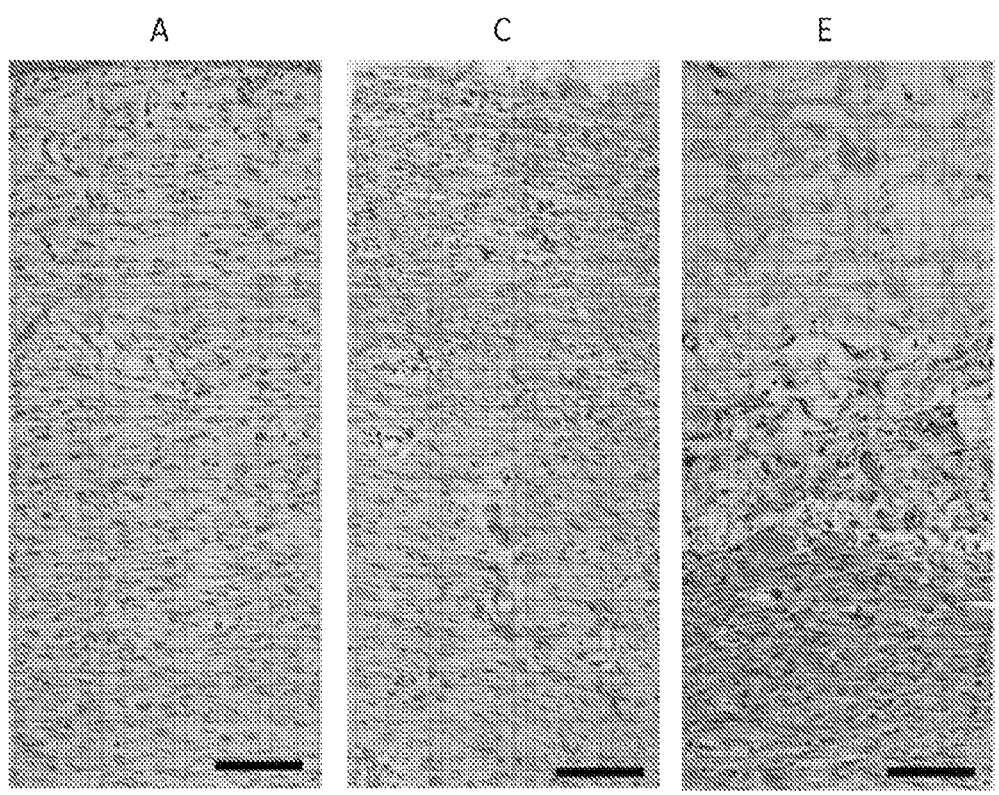

FIG. 11 is a set of microscopy images showing comparison of the wound healing status at day 28 post-operation. (A) normal skin control, (B) healed matrix of PCHM group, (C) healed matrix of Integra group.

Figure 12:
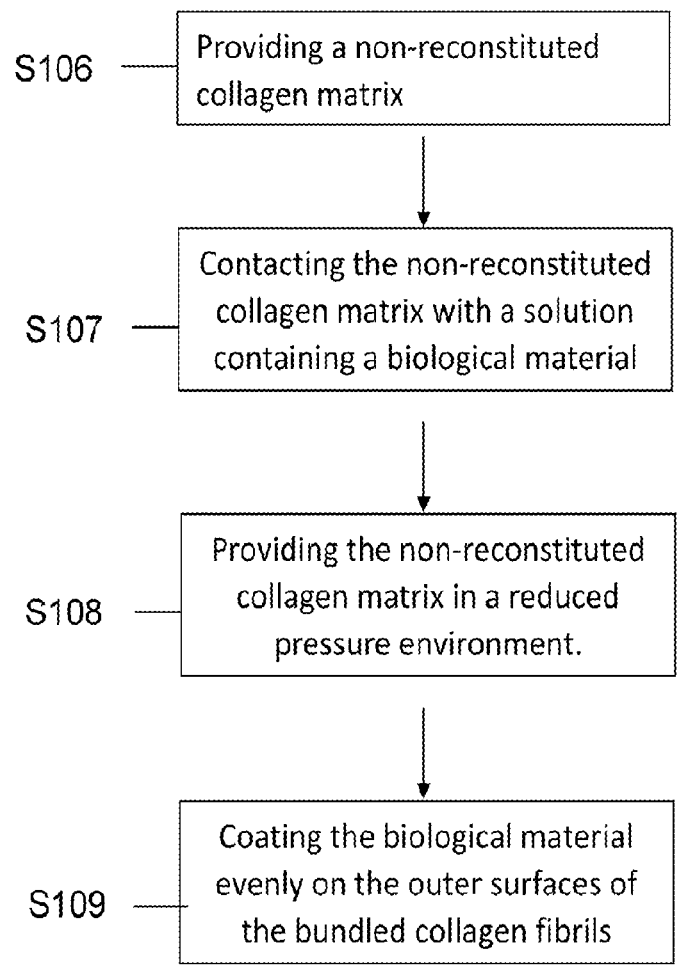

FIG. 12 is a flowchart showing a method for preparing a biological scaffold in an embodiment of the present invention.

Figure 13A:
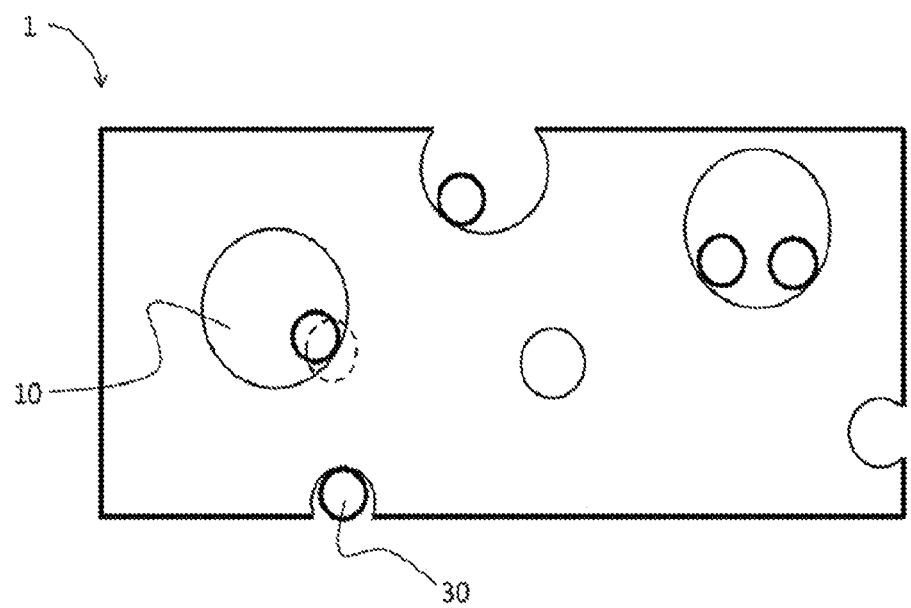
Figure 13B:
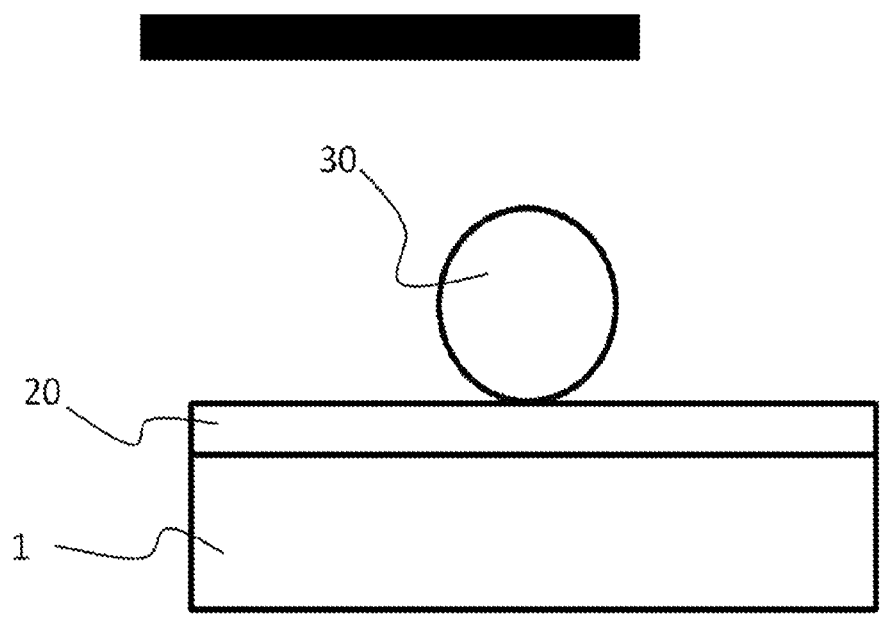

FIGS. 13A to 13B are schematic cross-sectional view and partial enlargement showing a biological scaffold according to another embodiment of the present invention.

Figure 14A:
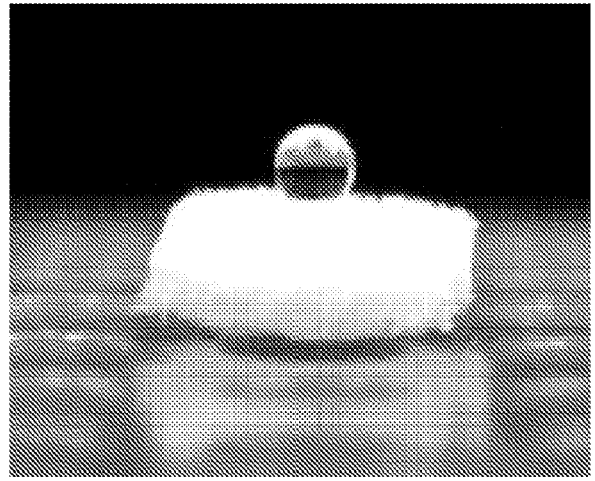
Figure 14B:
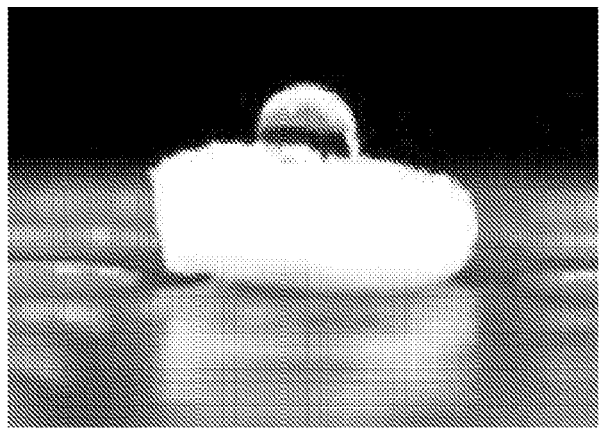
Figure 14C:
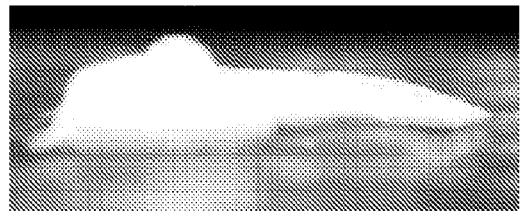

FIGS. 14A to 14C are comparison diagrams of water absorption capacity of biological scaffolds having different extent of biological material coating in an embodiment of the present invention.

FIGS. 15A to 15D show the antibacterial effect of the biological scaffolds covered with different antibacterial materials in an embodiment of the present invention.

DETAILED DESCRIPTION

Figure 1:
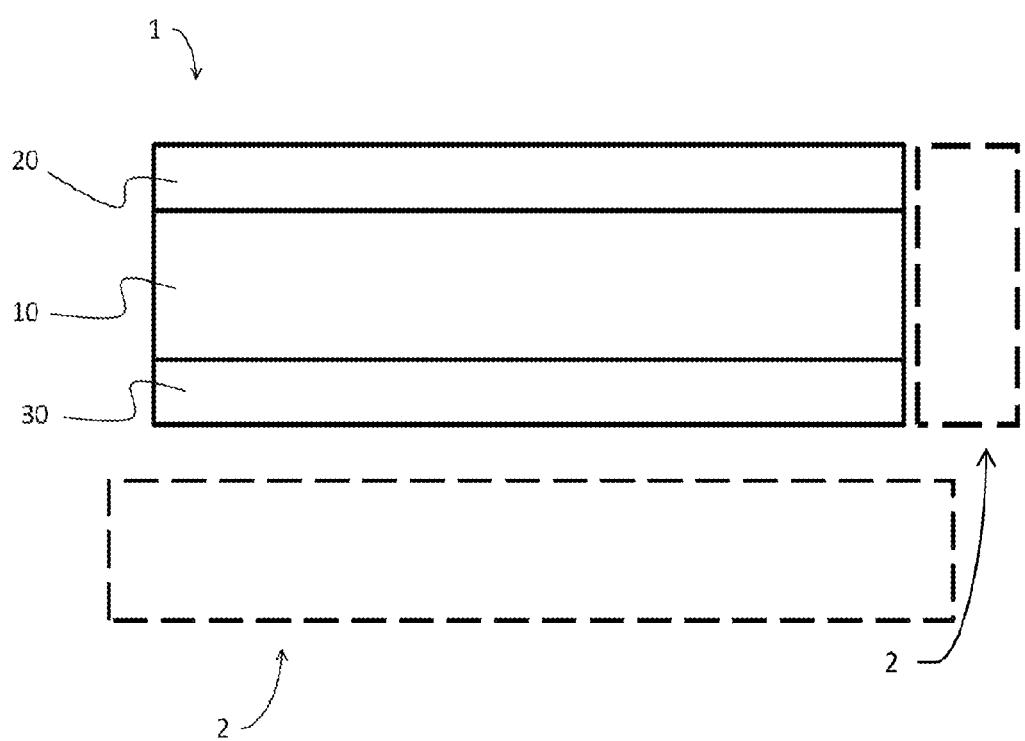
FIG. 1 is a schematic cross-sectional view showing a non-reconstituted biological scaffold in an embodiment of the present invention.

Referring to FIG. 1, the present invention provides a non-reconstituted material biological scaffold 1 which includes: a main body 10, a biological material layer 20, and a tissue adhesive layer 30. The main body 10 includes at least one non-reconstituted collagen matrix 10a. The biological material layer 20 and the tissue adhesive layer 30 are coated on one surface of the body and the adjacent or opposite surface of the body respectively. When the above-mentioned biological scaffold is adhered to a tissue 2 by the tissue adhesive layer, a plurality of cells are chemoattracted by the biological material and moved from the tissue adhesive layer to the biological material layer, and reconstruction of the tissue 2 is performed.

Figure 2:
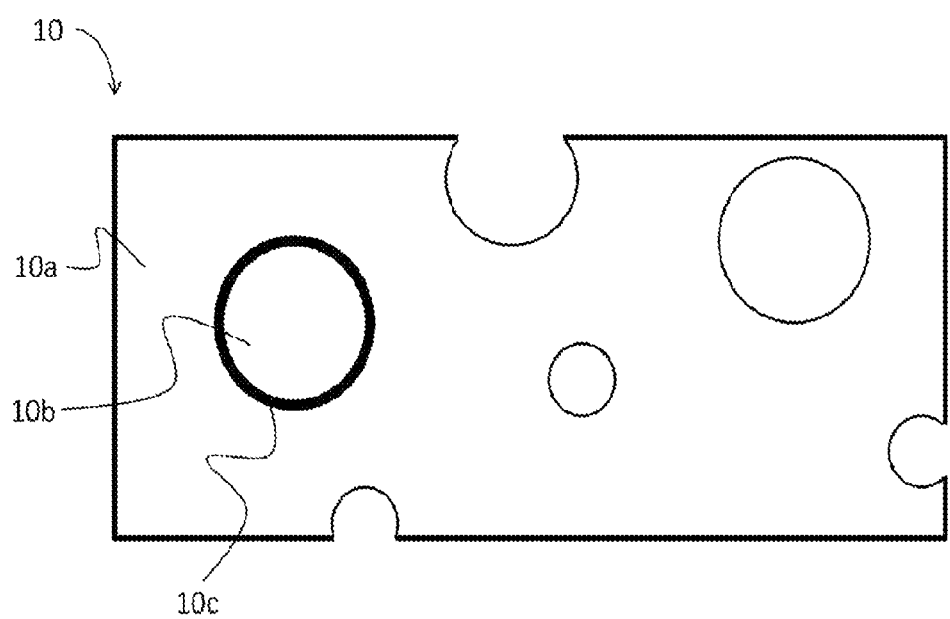
FIG. 2 is a schematic cross-sectional view showing the main body of a non-reconstituted biological scaffold in an embodiment of the present invention.

Referring to FIG. 2, which shows a schematic cross-sectional view of a main body 10 of a biological scaffold in an embodiment of the present invention. As shown in the figure, main body 10 is preferably a non-reconstituted collagen matrix 10a, and this collagen matrix 10a is composed of a plurality of columnar collagen fibrils and includes a plurality of pores 10b structured by collagen fibrils. A biological material 10c is coated on the inner surface of pores 10b.

Figure 4:
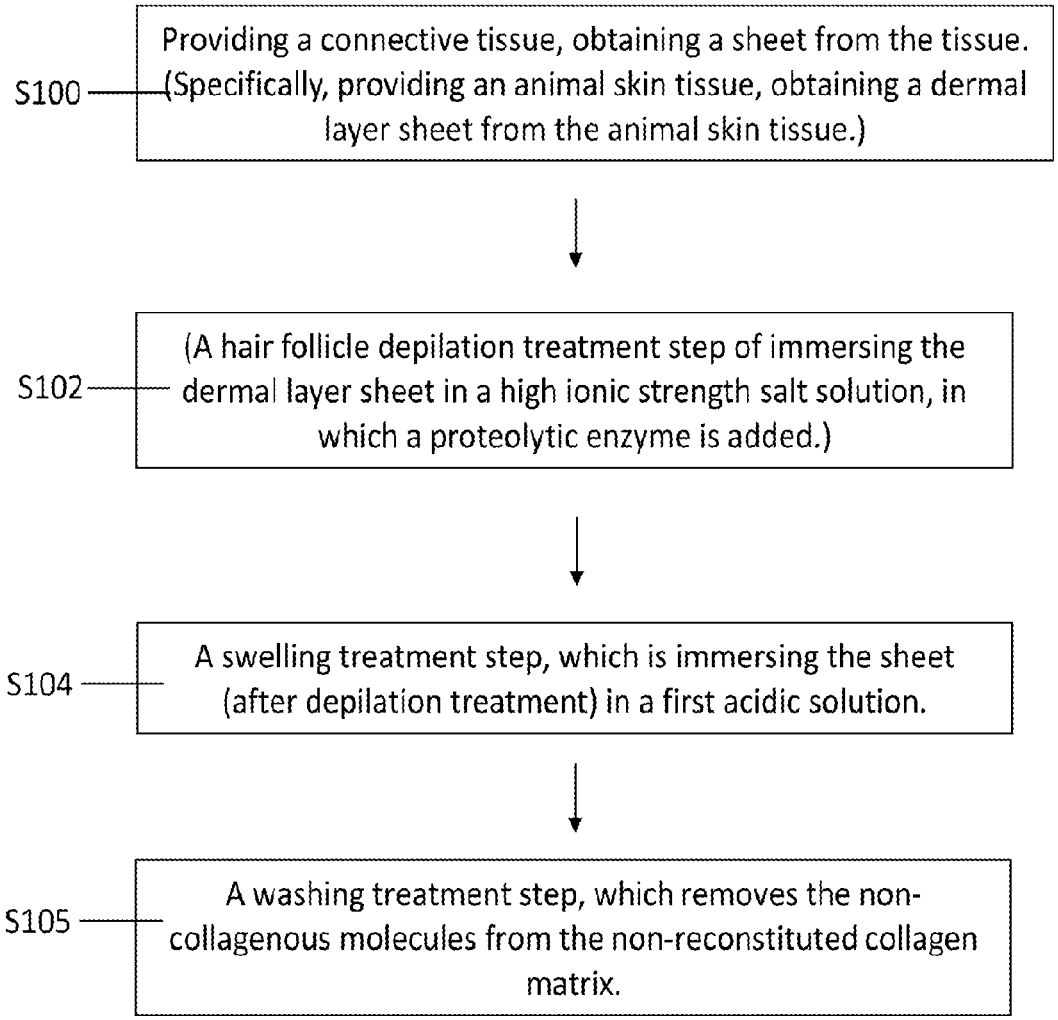
FIG. 4 shows a flow chart for preparation of a non-reconstituted collagen matrix of the present invention.

Referring to FIG. 4, a wound dressing prepared from a biological scaffold with a non-reconstituted collagen matrix of the present invention comprises: firstly, as shown in step S100, providing an animal tissue or an animal skin tissue, such as pig skin, cowhide, or sheepskin tissue, in an environment below 15° C., removing the subcutaneous fat of the animal skin tissue by a sharpener, and cutting the tissue to a size of 28±1 cm×70±1 cm. Next, the animal skin tissue was depilated and the oil and moisture remaining thereon were scraped off, and each skin tissue was cut into 4 pieces with each size at 13±1 cm×34±1 cm. Then, the dermal layer of the pig skin is peeled by a machine to obtain at least one dermal layer sheet, and then rinsed with pure water. Most preferably, the dermal layer is taken from pig skin.

Furthermore, as shown in step S102, a depilation treatment step is performed by immersing the dermal layer sheet in a salt solution containing high ionic strength, and after adding a proteolytic enzyme, heating the salt solution to 25-40° C. An ultrasonic oscillating treatment is then carried out for two hours. A phosphate buffered solution is used as a washing solution to clean the dermal layer sheet after the depilation treatment. A salt solution containing high ionic strength is a salt solution in which anion and cation are ionically bonded. The ionic strength of the salt solution containing high ionic strength is greater than 0.15 N. Most preferably, the ionic strength of the salt solution containing high ionic strength is between 0.5 N and 10 N. Most preferably, the salt solution containing high ionic strength is a solution containing a sodium chloride, ammonium sulfate, or a mixture of the above compounds.

In one embodiment, the salt solution containing high ionic strength is a phosphate buffered solution containing sodium chloride. This high salt condition stabilizes the structure of the non-reconstituted collagen matrix, does not cause the tissue to swell and is extruded into the hair follicle, so that the enzyme can smoothly enter the hair follicle for reaction.

In one embodiment, the proteolytic enzyme acts on the salt solution containing high ionic strength. Most preferably, the proteolytic enzyme is selected from the group consisting of serine proteases, threonine proteases, cysteine proteases, aspartate proteases, glutamate proteases, metalloproteases, and a combination of the above enzymes. Most preferably, the cysteine protease is selected from the group consisting of papaya enzymes, pineapple enzymes, and mixture of the above enzymes. Most preferably, the metalloprotease is dispase.

Referring to Table 1 below, when the dermal layer sheet was immersed with papain (a papaya enzyme) in a phosphate buffered solution containing ~5 mM or 0.16% (w/w) L-cysteine, and the concentration of papain was higher than 0.6 mg/mL (groups B, C, and D), the pig hairs were completely removed. When the dermal layer sheet was immersed with bromelain (a pineapple enzyme) in a phosphate buffered solution, and when the bromelain concentration was 0.2 mg/mL and 0.6 mg/mL (groups A and B), there was still pig hair that had not fallen off. When the concentration of bromelain was 1.2 mg/mL, the pig hairs were completely removed. The pig follicles could also be removed completely with more than 0.2 U/mL of dispase. As for the pigs in the control group (phosphate buffer only), all pig hair did not fall off.

TABLE 1

The dermal layer sheet (groups A-D) immersed in a phosphate buffered solution containing papain, bromelain, or dispase.

| Concentration | Groups | | | |
| --- | --- | --- | --- | --- |
|  | A | B | C | D |
| Papain (mg/mL) | 0.2 | 0.6 | 1.2 | 2.4 |
| Bromelain (mg/mL) | 0.2 | 0.6 | 1.2 | 2.4 |
| Dispase (U/mL) | 0.2 | 0.6 | 1.2 | 2.4 |

Referring to FIG. 4, as shown in step S104, a swelling treatment step is performed, in which the dermal layer sheet after depilation treatment is immersed in a first acidic solution, and the first acidic solution is heated to 33-37° C. with an ultrasonic oscillating treatment. The ultrasonic oscillating treatment time is continuous for 24 hours, so that the volume of the dermal layer sheet is expanded by at least fifty percent. Preferably, the first acidic solution is a weak acid solution selected from the group consisting of formic acid, carboxylic acid, oxalic acid, acetic acid, citric acid, lactic acid, malic acid, boric acid, phosphoric acid, hydrochloric acid, and a mixture thereof. Most preferably, the first acidic solution is an acetic acid solution.

As shown in step S105, a washing treatment step is performed to remove non-collagenous material from the dermal layer sheet and a purified collagen matrix is obtained. This follows with freezing the purified collagen matrix at −20° C. and −80° C., and a freeze-drying or lyophilization process to obtain a purified non-reconstituted porous collagen matrix.

Figure 5:
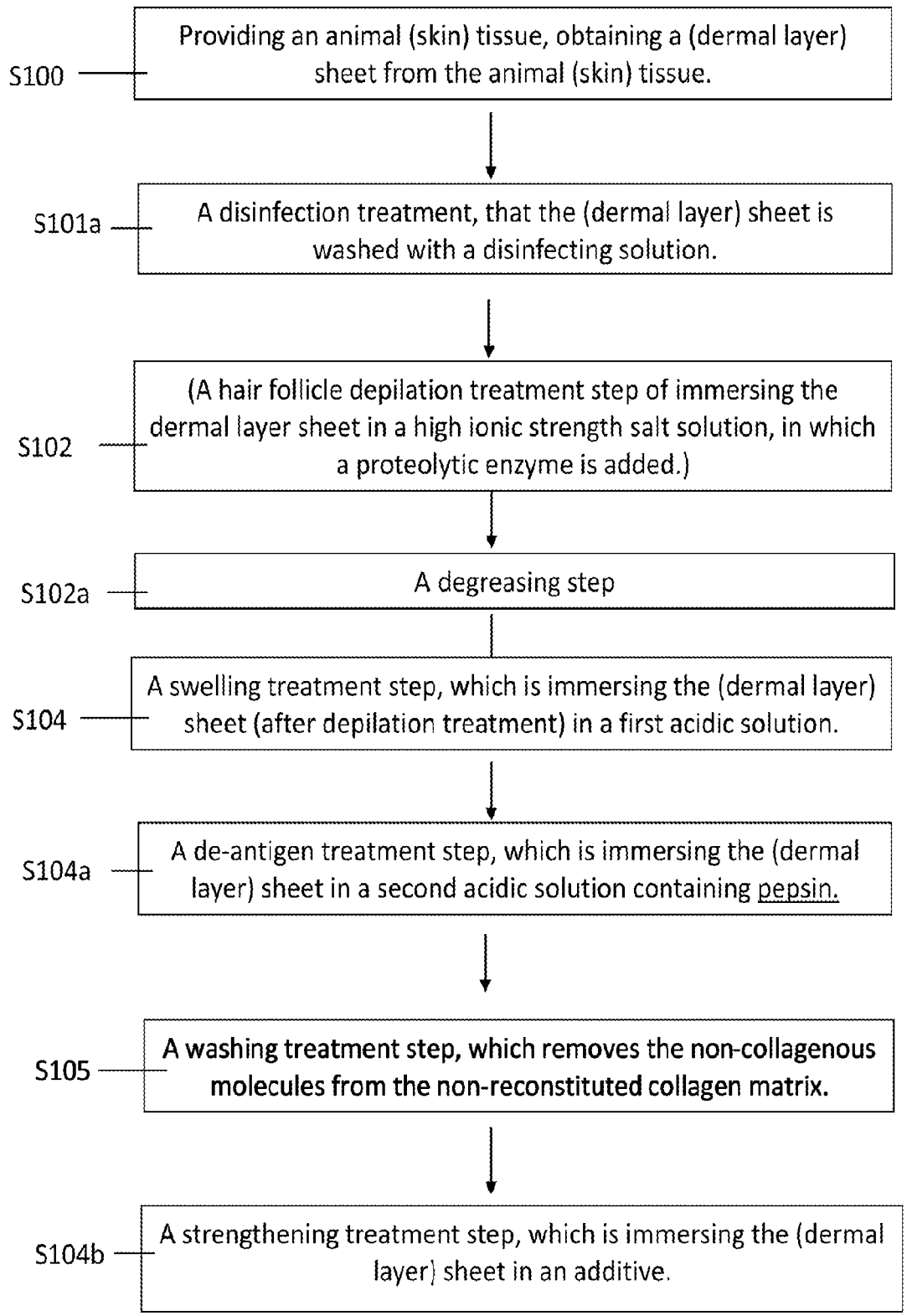
FIG. 5 shows another flow chart for preparation of a non-reconstituted collagen matrix of the present invention.

Referring to FIG. 5, which shows another embodiment of a preparation method of the non-reconstituted collagen matrix of the present invention, comprising: as shown in step S101a, a disinfection treatment before or after performing any step, in which the sheet or the dermal layer sheet is washed with a disinfecting solution. Most preferably, the disinfecting solution is a peracetic acid solution.

As shown in step S102a, the preparation method of the present invention further comprises a degreasing step before or after the depilation treatment step S102. The degreasing step is a saponification treatment, an organic solvent treatment, or a combination thereof. The saponification step is to contact the sheet or the dermal layer sheet with an alkaline substance, and one specific surface can be contacted if only one surface is greasing. Most preferably, the alkaline substance is in the form of granules of strong base particle. Most preferably, the strong base particles are sodium hydroxide particles. The organic solvent treatment is an alcohol treatment, a hexane treatment, or a chloroform treatment. Nevertheless, optimal amount and time period of treatment are required to prevent denaturation of collagen in the matrix.

As shown in step S104a, the preparation method of the present invention further comprises a de-antigen treatment step after the swelling treatment step S104. Most preferably, the de-antigen treatment step is to immerse the sheet or dermal layer sheet in a second acidic solution containing pepsin. The second acidic solution containing pepsin is heated to between 33° C. and 37° C. An ultrasonic oscillation treatment is then carried out for 4 hours. The solution remaining on the sheet or the dermal layer sheet is washed away with pure water. The sheet or dermal layer sheet is treated again with a potassium dihydrogen phosphate solution at 25° C. Preferably, the second acidic solution is a weak acid solution selected from the group consisting of formic acid, carboxylic acid, oxalic acid, acetic acid, citric acid, lactic acid, malic acid, boric acid, phosphoric acid, hydrochloric acid, and mixtures thereof. Most preferably, the second acidic solution is an acetic acid solution.

As shown in step S104b, the preparation method of the present invention further comprises a strengthening treatment step after the swelling treatment step, wherein a plurality of sheets or dermal layer sheets are laminated and immersed in an additive, preferably a crosslinking agent solution. The crosslinking agent solution is heated to between 33° C. and 37° C., and an ultrasonic oscillation treatment is performed for 24 hours to complete the crosslinking reaction. The remaining solution on the sheets or dermal layer sheets is rinsed off with pure water. Most preferably, one functional group of the cross-linking agent is selected from the group consisting of amine, sulfhydryl, carbonyl, glycol, hydroxyl, carboxyl, azide, imidoester, epoxide, aldehyde, haloacetyl, pyridyl disulfide, pyridyldithiol, hydrazide, photo-reacting, carbodiimide, diazirine, aziridine, acryloyl, arylate, thiol, genipin, riboflavin, flavonoid and its derivatives, hydroxymethyl phosphine, isocyanate, maleimide, 6-maleimidohexanoic acid active ester, disuccinimidyl suberate, bis(sulfosuccinimidyl)suberate, N-hydroxy-succinimide ester (NHS-ester), sulfosuccinimidyl-4-(N-maleimidomethyl)cyclohexane-1-carboxylate, pentafluorophenyl ester (PFP-ester), ethylene glycol diglycidyl ether, glutaraldehyde, 2,3-dibromopropionyl N-hydroxysuccinimide ester, sulfo-N-hydroxysuccinimide ester, chlorambucil-N-hydroxysuccinimide ester, 1-ethyl-3-(3-dimethylaminopropyl) carbodiimide, psoralen, vinyl sulfone, and a combination thereof.

Figure 6A:
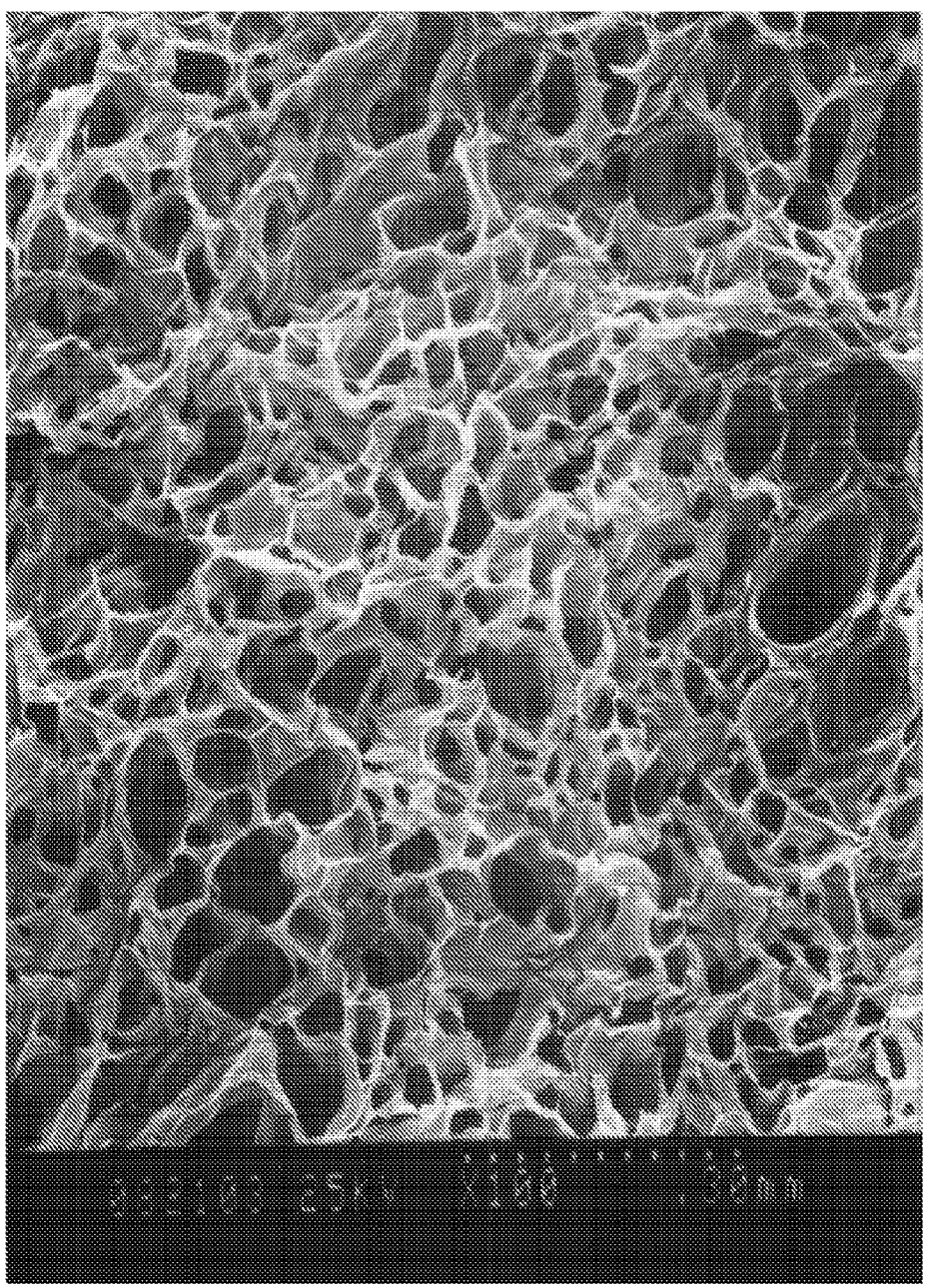
FIGS. 6A to 6C show electron microscope images of a non-reconstituted collagen matrix prepared by the method of the present invention.
Figure 6B:
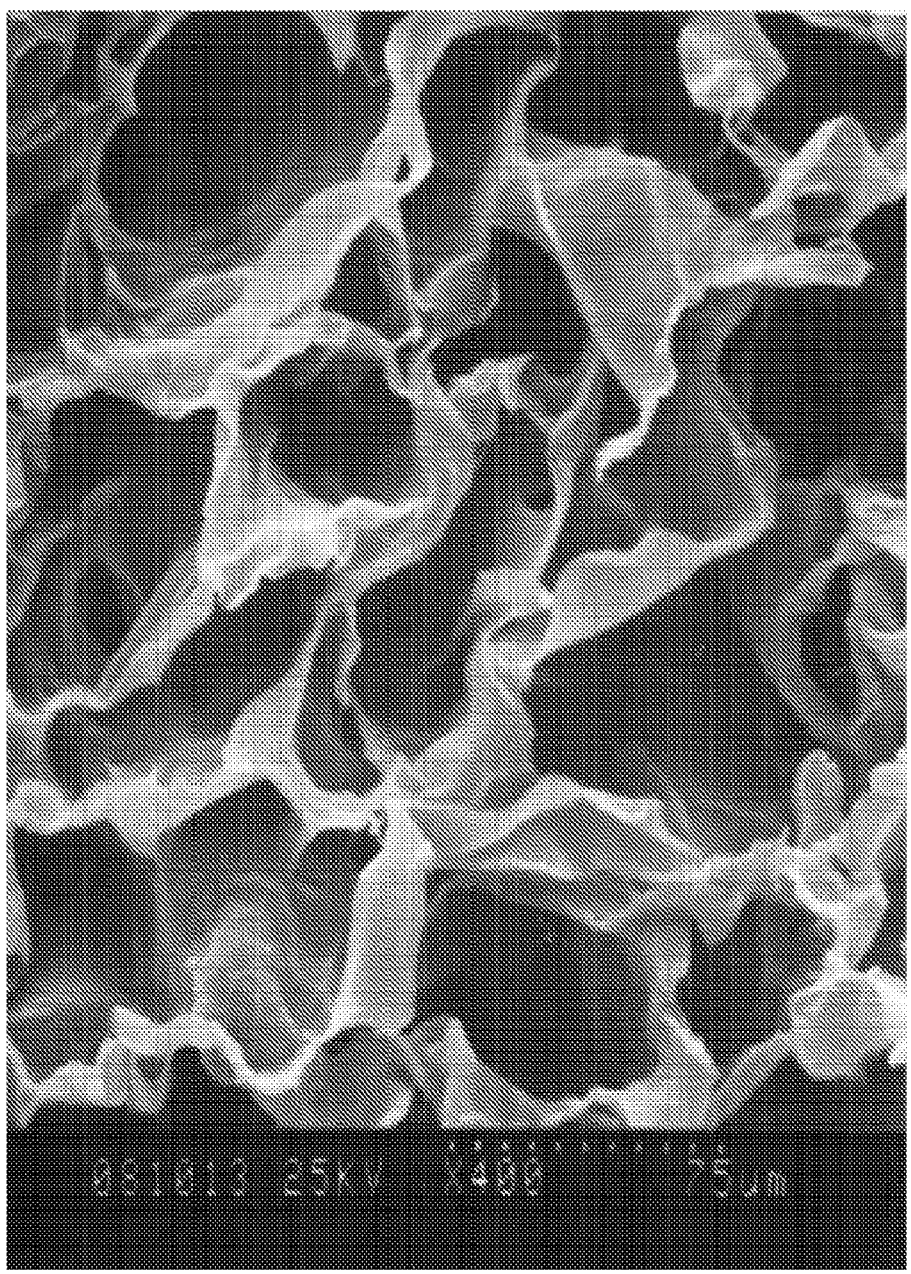
Figure 6C:
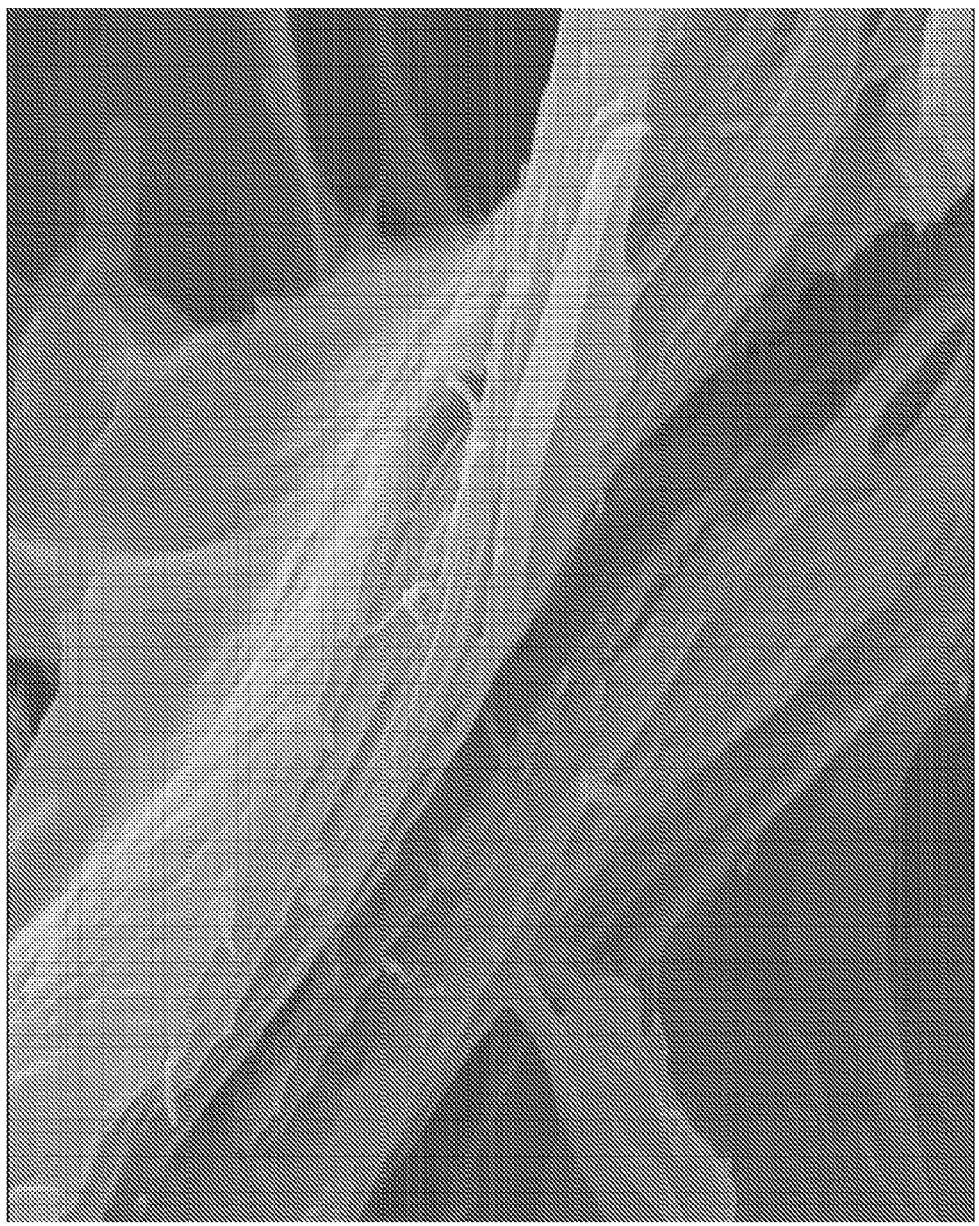

Referring to FIGS. 6A to 6C, which show the appearance of the non-reconstituted collagen matrix prepared according to the method described above. FIG. 6A is a 100× magnification image of a scanning electron microscope of a non-reconstituted collagen matrix in an embodiment of the present invention. FIG. 6B is a 400× magnification image of a scanning electron microscope of a non-reconstituted collagen matrix in an embodiment of the present invention. FIG. 6C is a 10,000× magnification of a scanning electron microscope of a non-reconstituted collagen matrix in an embodiment of the present invention.

Compared with the porous collagen matrix prepared by the prior art (see FIG. 3), the non-reconstituted porous collagen matrix prepared by the present invention is composed of a plurality of collagen fibril bundles interlaced and aggregated, and has a plurality of pores having a depth and having a groove wall. The above-mentioned collagen fibril bundles are composed of procollagen molecules and has a diameter of less than 100 nm, but the present invention is not intended to be limited thereto. The appearance of the pores is a random radius opening, and the aperture size is controlled to a narrower range. Thus, a collagen matrix prepared by the method described herein has a relatively uniform aperture.

Please refer to FIGS. 7A to 7C, which show the appearance of a biological scaffold made from a non-reconstituted collagen matrix prepared according to the method described above. FIG. 7A is a 100× magnification image of a scanning electron microscope of a biological scaffold in an embodiment of the present invention. FIG. 7B is a 400× magnification image of a scanning electron microscope of a biological scaffold in an embodiment of the present invention. FIG. 7C is an image of a light micrograph of a biological scaffold with hyaluronan pre-activated by CNBr and cross-linked to the non-reconstituted collagen matrix in an embodiment of the present invention. Alcian blue was used to stain for the presence of hyaluronan derivatives inside the scaffold after sectioning of the histological sample. The image indicates a well-distribution of hyaluronan derivatives inside the biological scaffold.

Referring to FIG. 8, which shows a shear stress test of a non-reconstituted porous collagen matrix (line B) according to an embodiment of the present invention and a conventional porous collagen matrix (line A) obtained by the prior art. It can be seen from the results that the shear stress of the porous collagen matrix obtained by the prior art was 63.56 e-03 MPa at a temperature of 20° C., and the shear stress of the non-reconstituted porous collagen matrix of the present invention was 189.07 MPa. Thus, it was demonstrated that, under the same test conditions, the shear strength of a non-reconstituted porous collagen matrix of the present invention is about 3 orders of magnitude higher than the porous collagen matrix of the prior art. Since the hair follicles can be completely removed at the beginning, the non-reconstituted porous collagen matrix is indeed superior in structure strength and tension than conventional porous collagen matrix. In summary, the present invention provides a process for preparing a non-reconstituted porous collagen matrix, which can destroy the hair follicle tissue without destroying the natural crosslinks of collagen in the dermis layer, thereby a porous matrix having a structural strength higher than that of the prior art is prepared.

Referring to FIGS. 9A and 9B, which shows the changes of storage modulus and loss modulus along with variation of oscillation strain monitored by a reometer. The storage modulus is an indication of a matrix's ability to store deformation energy in an elastic manner. This is directly related to the extent of cross-linking, the higher the degree of cross-linking the greater the storage modulus. FIG. 9A is the data of a non-reconstituted porous collagen matrix of the present invention, whereas FIG. 9B shows the data of a conventional reconstituted porous collagen matrix. A microstructure means that there are forces between the molecules or particles in the material. To break the microstructure, a force larger than the ones holding it is needed. When the applied force is smaller than the molecular or inter particle forces, then G' is larger than G"; the material has some capacity to store energy and should be able to return, to some extent, to its initial configuration before a mechanical force is applied. The material behaves as an elastic solid, although not an ideal one because some of the mechanical energy is dissipated. The results in FIGS. 9A and 9B indicate that the storage modulus of the non-reconstituted porous collagen matrix is higher than that of the reconstituted porous collagen matrix prepared by the prior art. Most native crosslinks in the non-reconstituted porous collagen matrix are preserved, whereas most native crosslinks are lost in the conventional reconstituted porous collagen matrix.

Furthermore, since the non-reconstituted collagen matrix 10*a* itself is not a hydrophilic material, the main body 10 may further include a hydrophilic biomaterial 10*c* coated on the outer surfaces of the collagen fibrils. That is, the inner walls of these pores 10*b* are also coated with a hydrophilic biological material 10*c* (as shown in FIG. 2) to facilitate the infiltration of cells into the non-reconstituted porous collagen matrix 10*a* and subsequently move and adhere/attach within it. Preferably, the above-mentioned biological material may be a growth factor or a glycosaminoglycan such as hyaluronan (HA), chondroitin sulfate (CS) or heparan (Hep).

More preferably, the hydrophilic biological material 10*c* is hyaluronan, but the present invention is not intended to be limited thereto.

Referring to FIG. 1 again, in a preferred embodiment of the present invention, the growth factor material layer 20 coated on one surface of main body 10 is selected from the group consisting of epidermal growth factor (EGF), fibroblast growth factor (FGF), vascular endothelial growth factor (VEGF), connective tissue growth factor (CTGF), platelet-derived growth factor (PDGF), insulin-like growth factor (IGF-I, IGF-II), nerve growth factor (NGF), hepatocyte growth factor (HGF), colony-stimulating factor (CSF), stem cell factor (SCF), keratinocyte growth factor (KGF), granulocyte colony-stimulating factor (GCSF), macrophage colony-stimulating factor (MCSF), granulocyte macrophage colony-stimulating factor (GMCSF), glial derived neurotrophic factor (GDNF), ciliary neurotrophic factor (CNF), endothelial-monocyte activating polypeptide, epithelial neutrophil activating peptide, erythropoietin, bone morphogenetic protein (BMP-1, BMP-2, BMP-3, etc.), brain-derived neurotrophic factor (BDNF), BRAK, serotonin, von Willebrand factor (vWF), transforming growth factor (TGF-α, TGF-β), interleukin (IL-1, IL-2, IL-3, etc.), tumor necrosis factor (TNF), and a combination thereof.

In addition, although tissue adhesives used in clinical medicine and tissue engineering, by virtue of their adhesive properties, they can achieve the effects of controlling drug release, regulating the breakdown of biocompatible materials, or promoting joint of blood vessels. However, because the tissue adhesives of the conventional techniques are made of cross-linking agents such as glutaraldehyde (GA), glyoxal, formaldehyde, or sodium tripolyphosphate (TPP) and cross-linked with carrier materials such as gelatin, chitosan or collagen, the cross-linking agent is cytotoxic and easily leads to a strong and sustained immune response, making tissue adhesives cytotoxic.

Therefore, in the present invention, a tissue adhesive layer 30 with better bonding strength and low cytotoxicity is used, which comprises at least one cross-linking agent, at least one matrix component and a quenching agent. The cross-linking agent is transglutaminase or has a functional group, and the matrix component is used for cross-linking with the cross-linking agent. The quenching agent is used to react with the functional group of the crosslinking agent to reduce the cytotoxicity.

In a preferred embodiment, the above-mentioned cross-linking agent is transglutaminase or one of its functional group is selected from a group consisting of reactive compounds containing amine, sulfhydryl, carbonyl, glycol, hydroxyl, carboxyl, azide, imidoester, epoxide, aldehyde, haloacetyl, pyridyl disulfide, pyridyldithiol, hydrazide, photo-reacting, carbodiimide, diazirine, aziridine, acryloyl, arylate, thiol, genipin, riboflavin, flavonoid and its derivatives, hydroxymethyl phosphine, isocyanate, maleimide, 6-maleimidohexanoic acid active ester, disuccinimidyl suberate, bis(sulfosuccinimidyl)suberate, N-hydroxy-succinimide ester (NHS-ester), sulfosuccinimidyl-4-(N-maleimidomethyl)cyclohexane-1-carboxylate, pentafluorophenyl ester (PFP-ester), ethylene glycol diglycidyl ether, glutaraldehyde, 2,3-dibromopropionyl N-hydroxysuccinimide ester, sulfo-N-hydroxysuccinimide ester, chlorambucil-N-hydroxysuccinimide ester, 1-ethyl-3-(3-dimethylaminopropyl) carbodiimide, psoralen, vinyl sulfone, and a combination thereof.

In a preferred embodiment, the matrix component is selected from the group consisting of collagen, hyaluronan, gelatin, silk fibroin, fibronectin, elastin, tenascin, laminin, vitronectin, heparan sulfate, chondroitin, chondroitin sulfate, keratin, keratan sulfate, dermatan sulfate, carrageenan, heparin, chitin, chitosan, alginate, aggrecan, agarose, agar, cellulose, methyl cellulose, carboxyl methyl cellulose, glycogen, fibrin, fibrinogen, thrombin, polyglutamic acid, polylysine, polyamino acid, synthetic polymers (e.g., acrylate, polylactic acid, polyglycolic acid, polylactic acid-glycolic acid), a derivative thereof, and a combination thereof.

More preferably, the matrix components can be prepared from any natively produced collagen or functional variants thereof and/or hyaluronan. Moreover, it has been shown that hyaluronan, especially high molecular weight hyaluronan (greater than 5 kDa), can effectively promote angiogenesis and further promote wound healing. For example, the molecular weight of hyaluronan can be 50 kDa to 5,000 kDa, 70 kDa to 1,500 kDa, 200 kDa to 1,500 kDa, 500 kDa to 1,500 kDa, or 700 kDa to 1,500 kDa. When cells grow in the matrix of collagen or hyaluronan, they have good viability. Therefore, in the matrix component of the tissue adhesive layer 30 used in the present invention, the concentration of hyaluronan is 0.001 mg/mL to 100 mg/mL and the concentration of collagen is 0.001 mg/mL to 100 mg/mL. Preferably, the concentration of collagen is 0.1 mg/mL to 100 mg/mL, and the concentration of hyaluronan is 0.01 mg/mL to 35 mg/mL. More preferably, the concentration of collagen is 3 mg/mL to 75 mg/mL (such as 6 mg/mL or 9 mg/mL), and the concentration of hyaluronan is 0.2 mg/mL to 20 mg/mL.

In a preferred embodiment, the quenching agent is selected from the group consisting of amino acid, oligopeptide, polypeptide, protein, amine, diamine, oligoamine, polyamine, carbonyl compound, glycol compound, carboxyl compound, dicarboxylate, oligo-carboxylate, polycarboxylate, sulfhydryl compound, oligosulfhydryl compound, polysulfhydryl compound, hydroxyl compound, oligohydroxyl compound, polyhydroxyl compound, saccharide, oligosaccharide, polysaccharides, ribonucleic acid (RNA), deoxyribonucleic acid (DNA), oligonucleotide, azide, photo-crosslinking compound, a monofunctional or heterobifunctional group, and a combination thereof. More preferably, the quenching agents used in the present invention include spermine, protamine, 1-6 hexanediamine, and polylysine, which is of different groups of varied molecular weights. The average molecular weights of polylysine are 3.4 kDa, 20 kDa, 99 kDa, 212 kDa, and 225 kDa, respectively.

FIG. 10A is a comparison diagram showing the healing of full-thickness wounds in the dorsal skin of guinea pigs implanted with Integral® artificial skin or PCMH. Integra® artificial skin, served as a control, is a reconstituted porous collagen-chondroitin sulfate matrix prepared by a conventional method with dehydrothermal crosslinking. PCHM is a biological scaffold of the present invention composed of a non-reconstituted porous collagen matrix and hyaluronan coated on the outer and inner surface of the matrix. A stable porous structure of PCHM allows a better infiltration of dermal cells up to 4 folds than the control group. Thus, the healing speed of the wounds filled with PCHM was demonstrated to be much faster (by about 80%) than that in the Integra group. The healing quality as demonstrated in the histology of regenerative matrix of the PCHM group was also much better than the control group at month 4 post-operation.

Referring to FIG. 11, at day 28 post-operation, in comparison with normal skin, the biological scaffold of PCHM has degraded within two weeks and the healed matrix of PCHM group was basically replaced with neomatrix, as histology indicated in FIG. 11B. As shown in FIG. 11C, some debris of Integra artificial skin was observed, which interfered with the regeneration process of wound healing.

Referring to FIG. 12, as shown in steps S106 to S109, the non-reconstituted collagen matrix is contacted with a solution containing a biological material, and the non-reconstituted collagen matrix is provided in a reduced pressure environment. In one embodiment, one end of the non-reconstituted collagen matrix is placed in a solution containing at least one biological material. A reduced pressure environment is created at the other end of the non-reconstituted collagen matrix so that the biological material can be absorbed into the structure of the non-reconstituted collagen matrix to allow the biological material to be evenly coated on the outer and inner surfaces of the bundled collagen fibrils (can also be considered as being evenly coated on the inner walls of the pores), as shown in step S108. It must be noted that, because the porous diameter of the non-reconstituted collagen matrix is extremely small, it is impossible to avoid air residue by merely immersing the non-reconstituted collagen matrix in the solution. Therefore, in the present invention, the principle of siphon is used to indirectly remove air, so that the biological material can completely cover the outer surfaces of the bundled collagen fibrils (also can be regarded as the inner walls of the pores). In addition, the above-mentioned reduced pressure environment is preferably performed by a vacuuming action.

The above-mentioned biological material is selected from the group consisting of a cell attachment material, a tissue repair material, a cell induction material, a growth factor material, an antibacterial material, and a combination thereof. Preferably, the above-mentioned cell attachment material is a saccharide, a peptide, a protein, a phospholipid, or a combination thereof. Preferably, the saccharide material is a glycosaminoglycan material. Preferably, the glycosaminoglycan material is selected from the group consisting of chondroitin, chondroitin sulfate, heparin, heparan sulfate, heparan sulfate proteoglycan, keratin, keratan sulfate, dermatan sulfate, carrageenan, hyaluronan, and a combination thereof. Preferably, the biomaterial used in the present invention is selected from the group consisting of collagen, elastin, glycosaminoglycan, chitosan, alginate, polyglutamic acid (γ-PGA), polylysine, poly(lactic-co-glycolic acid) PLGA, silk protein, and fibroin, but the present invention is not intended to be limited thereto.

Preferably, the cell induction material is selected from the group consisting of molecules such as vitamins, minerals, growth factors, chemicals, medicine, herbal medicine, metabolites, intermediate metabolites, a saccharide, a peptide, a protein, a phospholipid, or a combination thereof.

Preferably, the growth factor material is selected from the group consisting of epidermal growth factor (EGF), fibroblast growth factor (FGF), vascular endothelial growth factor (VEGF), connective tissue growth factor (CTGF), platelet-derived growth factor (PDGF), insulin-like growth factor (IGF-I, IGF-II), nerve growth factor (NGF), hepatocyte growth factor (HGF), colony-stimulating factor (CSF), stem cell factor (SCF), keratinocyte growth factor (KGF), granulocyte colony-stimulating factor (GCSF), macrophage colony-stimulating factor (MCSF), granulocyte macrophage colony-stimulating factor (GMCSF), glial derived neurotrophic factor (GDNF), ciliary neurotrophic factor (CNF), endothelial-monocyte activating polypeptide, epithelial neutrophil activating peptide, erythropoietin, bone morphogenetic protein (BMP-1, BMP-2, BMP-3, etc.), brain-derived neurotrophic factor (BDNF), BRAK, serotonin, von Willebrand factor (vWF), transforming growth factor (TGF-α, TGF-β), interleukin (IL-1, IL-2, IL-3, etc.), tumor necrosis factor (TNF), and a combination thereof.

Preferably, the antibacterial material is an antibiotic, an antimicrobial protein, an antimicrobial peptide, or a combination thereof.

For the detailed structure of the non-reconstituted collagen matrix please refer to FIG. 2, which is a schematic cross-sectional view of a biological scaffold according to an embodiment of the present invention. As shown above, the non-reconstituted collagen matrix 10a is composed of a plurality of bundled collagen fibrils which includes a plurality of pores 10b. The biological material 10c is absorbed into the non-reconstituted collagen matrix 10a by the principle of siphon and is coated on the outer surface of the bundled collagen fibrils. That is, the inner walls of the pores 10b are all coated with biological material 10c, which is more conductive for cells to enter the pores and adhere to the biological material for subsequent applications.

In a preferred embodiment of the present invention, although not shown in FIG. 2, after the biological material is coated on the outer surfaces of the bundled collagen fibrils, cells can be introduced into the biological scaffold. A cell culture medium or a solution containing cells is injected into the pores 10b to allow the cells to enter the pores of the non-reconstituted collagen matrix. That is, in a preferred embodiment of the present invention, the biological scaffold provided by the present invention further includes cells, as shown in FIG. 13A. Referring to FIG. 13B, which is a partially enlarged view of the dotted lined circle in FIG. 13A, in which the cells 30 are attached to the biological material 10c in the pore 10b. Preferably, the cells may be stem cells, satellite cells, precursor cells, progenitor cells, or tissue cells, and the tissue cells may also include skin tissue, cartilage tissue, or adipose tissue, and so on.

Table 2 below shows the comparison of the number of adhered cells of a non-reconstituted collagen matrix without biological material and non-reconstituted collagen matrix with biological material in different fields of vision. As can be seen from Table 2, the non-reconstituted collagen matrix itself is a hydrophobic material, which is not conductive for adherence of cells into the pores. However, when the present invention further coats the surface of the non-reconstituted collagen matrix with a cell attachment material, it was shown to be beneficial for subsequent cells to enter these pores and adhere to the biological scaffold.

TABLE 2

| number Field | Cell | |
|---|---|---|
| | Non-reconstituted collagen matrix without biological material | Non-reconstituted collagen matrix coated with biological material |
| 1 | 1 | 24 |
| 2 | 4 | 24 |
| 3 | 1 | 10 |
| 4 | 0 | 5 |
| 5 | 3 | 0 |
| 6 | 1 | 3 |
| Average | 1.67 | 11.00 |
| Standard Deviation | 1.51 | 10.58 |

Next, water absorption of a non-reconstituted collagen matrix (A1) without biological material, a non-reconstituted collagen matrix (A2) coated with hyaluronan (once), and a non-reconstituted collagen matrix (A3) coated with hyaluronan (five times) were further compared. See FIGS. 14A to 14C. The three figures show the water absorption conditions of A1, A2, and A3, respectively. Therefore, it was demonstrated that the non-reconstituted collagen matrix coated with more layers of biological materials has better water absorption capacity.

The effect of the biological scaffold used in wound dressings provided by the present invention was confirmed. See FIGS. 10B and 11. FIG. 10B compares the wound healing time of different biological scaffolds, and FIG. 11 compares the wound healing status of different biological scaffolds.

First, FIG. 10B shows different treatments of the wound, which were divided into groups A, B, C, D, and E to observe the relationship between the wound area and healing time. Among them, the initial wound area was 100%, and it was measured every two days until the wounds were completely healed. A represented an untreated wound, B represented a wound treated with a porous collagen matrix (PCM), C represented a wound treated with CNBr-activated hyaluronan (aH) combined porous collagen matrix (PCM-aH), D represented a wound treated with PCM-aH with an additional 5 mg/mL of hyaluronan, and E represented a wound treated with Integra® artificial skin. As shown in the figure, the wounds of group B, group C and group D all healed in about 30 days, but the wounds treated with artificial skin (group E) took 44 days to heal. Although group A healed slightly faster, it showed wound contraction and other conditions.

As shown in FIG. 10B, after 12 days, the fibroblast proliferation status of group C (wound treated with PCM-aH) did indeed exceed that of group E (wound treated with artificial skin). It was thus shown that the above-mentioned main body 10 combined with biological materials can effectively promote cell proliferation without causing wound contraction and can heal wounds more quickly than the artificial skin of the conventional technology.

Figure 15A:
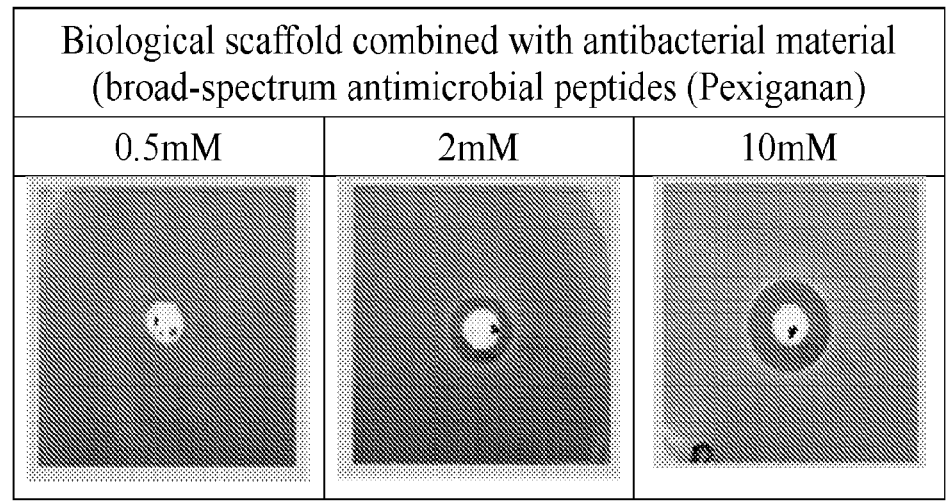
Figure 15B:
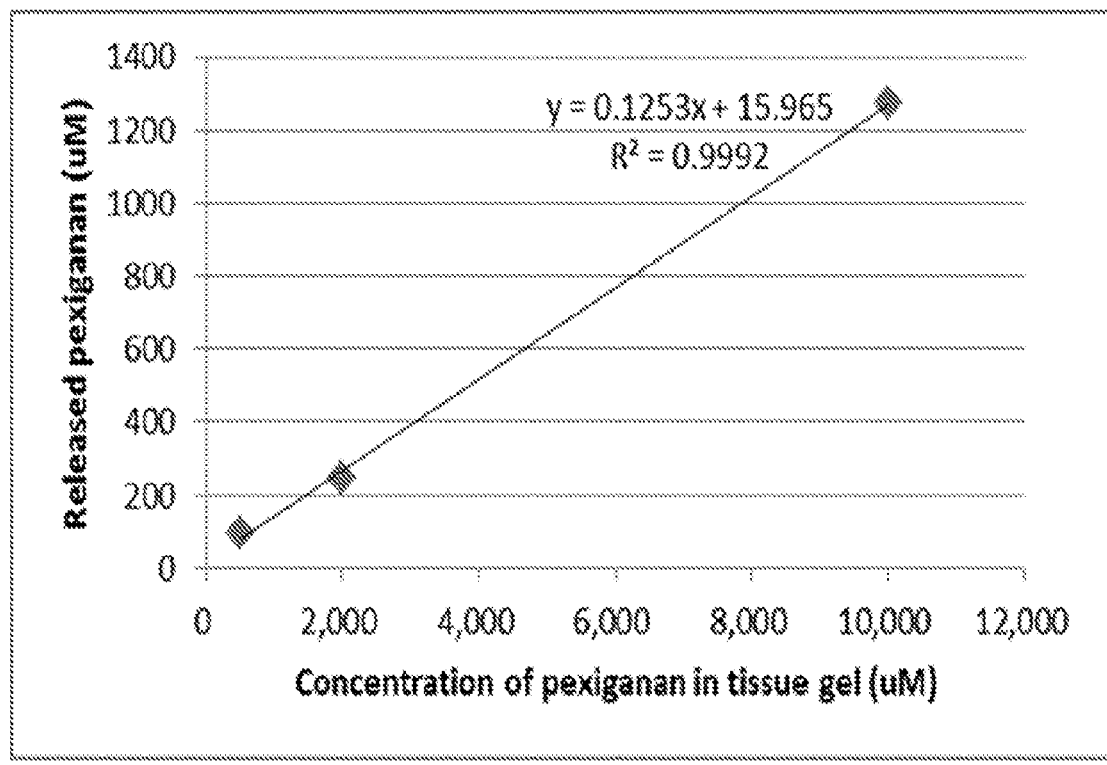
Figure 15C:
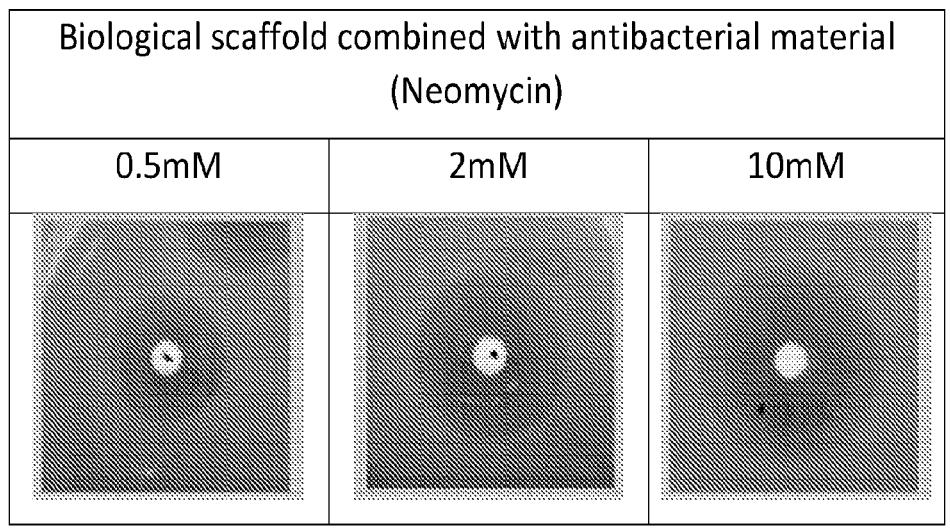
Figure 15D:
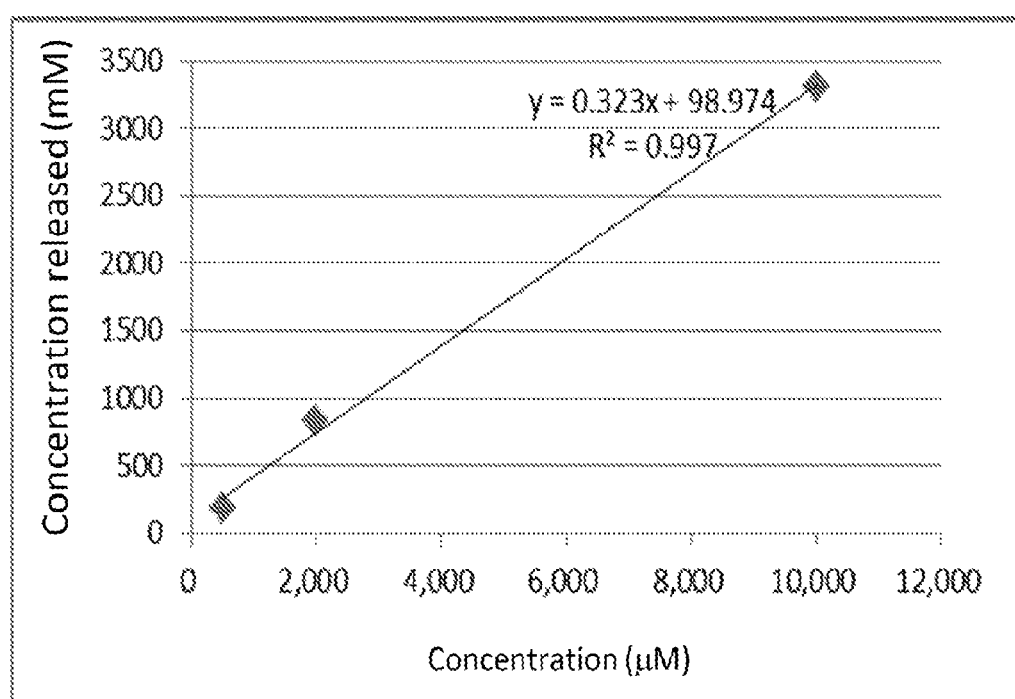

Next, in another embodiment, as shown in FIGS. 15A-15D, the biological scaffold was coated with different antibacterial materials, such as with anti-microbial peptide Pexiganan in FIGS. 15A and 15B and with neomycin in FIGS. 15C and 15D. The results showed that the antibacterial effect was concentration-dependent, and the biological scaffolds coated with antibacterial material had a good antibacterial effect.

In summary, a purpose of the present invention is to provide a biological scaffold that can be used in wound dressings. In one embodiment, one side of the main body is coated with a layer of biological material, and another side is coated with a tissue adhesive layer which allows cells to move within the main body based on the effect of concentration gradients. Furthermore, because the main body contains hydrophilic biological materials, it can further facilitate the movement and attachment of cells. Therefore, in addition to effectively blocking foreign bacterial invasion to prevent wound infection, the biological scaffold provided by the present invention can also be used to accelerate cell growth and promote the speed of wound healing.

Figure 3:
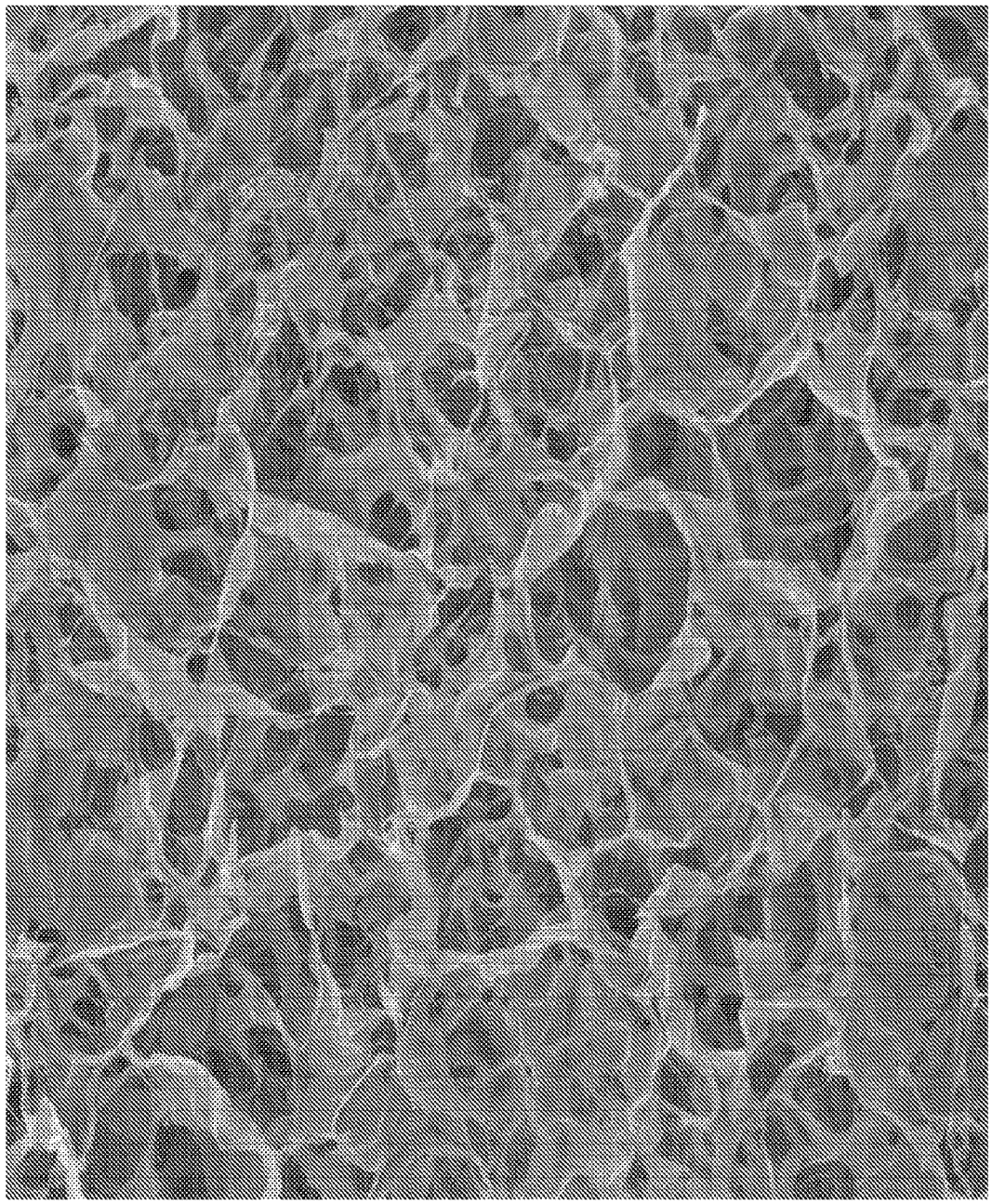
FIG. 3 shows a 100× magnified electron microscope image of a conventional reconstituted porous collagen matrix.

Furthermore, although it is known in conventional techniques to add minced collagen to biological material (such as hyaluronan) and then cross-linking them to coagulate into a structure, as collagen and biological materials become intertwined, the outside of the biological scaffold is not entirely hydrophilic. In addition, if a reconstituted collagen scaffold is first made ready (as shown in FIG. 3) and then subjected to the method provided by the present invention, the support force of the reconstituted collagen matrix would be insufficient (see FIG. 9 and the related description above)

to withstand the external pressure exerted by the vacuuming step, which is required in the subsequent coating of the scaffold with a biological material. As described above, the principle of siphon is applied so that the biological material can be completely absorbed or introduced into the non-reconstituted collagen matrix and uniformly coats the surface, so that the surface of the biological scaffold is favorable for cell infiltration and attachment. This biological scaffold can be widely applied in surgery, repair of human organs and tissues, regenerative medicine, skin transplantation or cosmetic medicine, and can also be used for surgical repair mesh fabric, dental repair mesh fabric, human skin substitute, artificial meningeal substitute, orthopedic repair substitute or wound dressing substitute.

The above detailed description is the specific description of certain feasible embodiments of the present invention, but these embodiments are not intended to limit the patent scope of the present invention. Any equivalent implementation or change that does not depart from the technical spirit of the present invention should be included within the patent scope of the present invention. All publications cited herein are herein incorporated by reference in their entirety.

DESCRIPTION OF SYMBOLS 1 biological scaffold
10 main body
10a non-reconstituted collagen matrix
10b pores
10c biological material
20 biological material layer
30 tissue adhesive layer
2 tissue
S100~S105 Method for preparing non-reconstituted collagen matrix
S100~S104b Method for preparing non-reconstituted collagen matrix
S106~S109 Preparation of biological scaffold

What is claimed is:

1. A biological scaffold, comprising:
a main body including a de-antigenic, non-reconstituted collagen matrix, wherein the non-reconstituted collagen matrix contains a plurality of bundled collagen fibrils that are interwoven and overlapped and a plurality of pores formed by the bundled collagen fibrils; and
a biological material coating a first outer surface and inside the plurality of pores of the main body, optionally, the biological material substantially coats the entire surface and inside of the main body;
wherein the non-reconstituted collagen matrix is prepared by a procedure including:
providing a layer sheet from an animal connective tissue;
carrying out a swelling step including immersing the layer sheet in a first acidic solution for a sufficient period of time to let the layer sheet form a swelled sheet layer, whereby forming a non-reconstituted collagen matrix; and
carrying out a de-antigen treatment step including immersing the non-reconstituted collagen matrix in a second acidic solution containing pepsin.

2. The biological scaffold of claim 1, wherein the biological material is selected from the group consisting of a cell attachment material, a tissue repair material, a cell induction material, a growth factor material, an antibacterial material, and a combination thereof.

3. The biological scaffold of claim 2, wherein:
the cell attachment material is a saccharide, a peptide, a protein, a phospholipid, or a combination thereof, optionally, the saccharide material is a glycosaminoglycan material.

4. The biological scaffold of claim 3, wherein the glycosaminoglycan material is chondroitin, chondroitin sulfate, heparin, heparan sulfate, heparan sulfate proteoglycan, keratan, keratan sulfate, dermatan sulfate, carrageenan, hyaluronan, or a combination thereof.

5. The biological scaffold of claim 2, wherein the growth factor material is epidermal growth factor (EGF), fibroblast growth factor (FGF), vascular endothelial growth factor (VEGF), connective tissue growth factor (CTGF), platelet-derived growth factor (PDGF), insulin-like growth factor (IGF-I, IGF-II), nerve growth factor (NGF), hepatocyte growth factor (HGF), colony-stimulating factor (CSF), stem cell factor (SCF), keratinocyte growth factor (KGF), granulocyte colony-stimulating factor (GCSF), macrophage colony-stimulating factor (MCSF), granulocyte macrophage colony-stimulating factor (GMCSF), glial derived neurotrophic factor (GDNF), ciliary neurotrophic factor (CNF), endothelial-monocyte activating polypeptide, epithelial neutrophil activating peptide, erythropoietin, bone morphogenetic protein, brain-derived neurotrophic factor (BDNF), BRAK, serotonin, von Willebrand factor (vWF), transforming growth factor, interleukin, tumor necrosis factor (TNF), or a combination thereof.

6. The biological scaffold of claim 2, wherein the cell induction material is a vitamin, mineral, chemical, medicine, herbal medicine, metabolite, intermediate metabolite, saccharide, peptide, protein, phospholipid, or a combination thereof.

7. The biological scaffold of claim 2, wherein the tissue repair material is a biomaterial, an extracellular matrix, a nutrient, or a combination thereof; optionally, the biomaterial is collagen, gelatin, hyaluronan, elastin, glycosaminoglycan, chitosan, alginate, polyglutamic acid (γ-PGA), polylysine, poly(lactic-co-glycolic acid) (PLGA), silk fibroin, polyamino acid, cellulose and its derivatives, or a combination thereof; optionally, the extracellular matrix is collagen, gelatin, elastin, glycosaminoglycan, proteoglycan, glycoprotein, fibronectin, laminin, aggrecan, metalloproteinase, or a combination thereof.

8. The biological scaffold of claim 2, wherein the antibacterial material is an antibiotic, an antimicrobial protein, an antimicrobial peptide, or a combination thereof.

9. The biological scaffold of claim 2, wherein the biomaterial is collagen, gelatin, hyaluronan, elastin, glycosaminoglycan, chitosan, alginate, polyglutamic acid (γ-PGA), polylysine, poly(lactic-co-glycolic acid) (PLGA), silk fibroin, polyamino acid, cellulose or a derivative thereof, or a combination thereof.

10. The biological scaffold of claim 1, further comprising cells in the plurality of the pores in the main body, optionally, the cells are stem cells, satellite cells, progenitor cells, precursor cells, or tissue cells.

11. The biological scaffold of claim 10, further comprising a cell medium in the plurality of pores, wherein the cells are attached to the biological scaffold.

12. The biological scaffold of claim 1, further comprising a tissue adhesive layer coated on a second surface of the main body.

13. The biological scaffold of claim 12, wherein the tissue adhesive layer includes:
a cross-linking agent having at least a functional group; and a quenching agent for reacting with any excess functional group of the crosslinking agent that has not reacted.

14. The biological scaffold of claim 13, wherein the cross-linking agent is transglutaminase or has a functional group selected from the group consisting of amine, sulfhydryl, carbonyl, glycol, hydroxyl, carboxyl, azide, imidoester, epoxide, aldehyde, haloacetyl, pyridyl disulfide, pyridyldithiol, hydrazide, photo-reacting, carbodiimide, diazirine, aziridine, acryloyl, arylate, thiol, genipin, riboflavin, flavonoid and its derivatives, hydroxymethyl phosphine, isocyanate, maleimide, 6-maleimidohexanoic acid active ester, disuccinimidyl suberate, bis(sulfosuccinimidyl)suberate, N-hydroxy-succinimide ester (NHS-ester), sulfosuccinimidyl-4-(N-maleimidomethyl)cyclohexane-1-carboxylate, pentafluorophenyl ester (PFP-ester), ethylene glycol diglycidyl ether, glutaraldehyde, 2,3-dibromopropionyl N-hydroxysuccinimide ester, sulfo-N-hydroxysuccinimide ester, chlorambucil-N-hydroxysuccinimide ester, 1-ethyl-3-(3-dimethylaminopropyl) carbodiimide, psoralen, vinyl sulfone, and a combination thereof.

15. The biological scaffold of claim 13, wherein the tissue adhesive layer further includes a matrix molecule cross-linked with the cross-linking agent, and wherein the matrix molecule is selected from the group consisting of collagen, hyaluronan, gelatin, silk protein, fibroin, fibronectin, elastin, tenascin, laminin, vitronectin, heparan sulfate, chondroitin, chondroitin sulfate, keratin, keratan sulfate, dermatan sulfate, carrageenan, heparin, chitin, chitosan, alginate, aggrecan, agarose, agar, cellulose, methyl cellulose, carboxyl methyl cellulose, glycogen, fibrin, fibrinogen, thrombin, polyglutamic acid, polylysine, polyamino acid, synthetic polymers, a derivative thereof, and a combination thereof.

16. The biological scaffold of claim 13, wherein the quenching agent is selected from the group consisting of amino acid, oligopeptide, polypeptide, protein, amine, diamine, oligoamine, polyamine, carbonyl compound, glycol compound, carboxyl compound, dicarboxylate, oligocarboxylate, polycarboxylate, sulfhydryl compound, oligosulfhydryl compound, polysulfhydryl compound, hydroxyl compound, oligohydroxyl compound, polyhydroxyl compound, saccharide, oligosaccharide, polysaccharides, ribonucleic acid (RNA), deoxyribonucleic acid (DNA), oligonucleotide, azide, photo-crosslinking compound a monofunctional or heterobifunctional group, and a combination thereof.

17. The biological scaffold of claim 1, wherein the layer sheet is a dermal layer sheet obtain from an animal skin tissue, and wherein the procedure further includes, before the swelling step, carrying out a depilating step that includes immersing the dermal layer sheet in a high ionic strength salt solution and then adding a proteolytic enzyme to the salt solution, whereby a depilated layer sheet is produced.

18. The biological scaffold of claim 17, wherein the procedure further includes a disinfection step or a degreasing step before or after the depilation step.

19. The biological scaffold of claim 17, wherein the procedure further includes, after the swelling step, a strengthening step that includes immersing the swelled dermal sheet layer in an additive; optionally, the additive is a crosslinking agent solution.

20. The biological scaffold of claim 1, wherein the procedure for preparing the non-reconstituted collagen matrix substantially preserves native crosslinks of collagen in the layer sheet, and the non-reconstituted collagen matrix substantially retains the native crosslinks of collagen in the layer sheet.

* * * * *